(12) United States Patent
Iazikov et al.

(10) Patent No.: US 7,327,908 B1
(45) Date of Patent: Feb. 5, 2008

(54) INTEGRATED OPTICAL SENSOR INCORPORATING SETS OF DIFFRACTIVE ELEMENTS

(75) Inventors: Dmitri Iazikov, Springfield, OR (US); Christoph M. Greiner, Eugene, OR (US); Thomas W. Mossberg, Eugene, OR (US)

(73) Assignee: LightSmyth Technologies Inc., Eugene, OR (US)

( * ) Notice: Subject to any disclaimer, the term of this patent is extended or adjusted under 35 U.S.C. 154(b) by 0 days.

(21) Appl. No.: 11/371,339

(22) Filed: Mar. 7, 2006

Related U.S. Application Data

(60) Provisional application No. 60/659,146, filed on Mar. 7, 2005.

(51) Int. Cl.
  *G02B 6/00* (2006.01)
  *G02B 6/34* (2006.01)
(52) U.S. Cl. .............................. 385/12; 385/13; 385/37
(58) Field of Classification Search ................... 385/12, 385/13, 37
  See application file for complete search history.

(56) References Cited

U.S. PATENT DOCUMENTS

| | | |
|---|---|---|
| 3,995,937 A | 12/1976 | Baues et al. |
| 4,006,967 A | 2/1977 | Kenan et al. |
| 4,140,362 A | 2/1979 | Tien |
| 4,387,955 A | 6/1983 | Ludman et al. |
| 4,440,468 A | 4/1984 | Auracher et al. |
| 4,660,934 A | 4/1987 | Akiba et al. |
| 4,740,951 A | 4/1988 | Lizet et al. |
| 4,743,083 A | 5/1988 | Schimpe |
| 4,746,186 A | 5/1988 | Nicia |
| 4,773,063 A | 9/1988 | Hunsperger et al. |
| 4,786,133 A | 11/1988 | Gidon et al. |
| 4,824,193 A | 4/1989 | Maeda et al. |
| 4,834,474 A | 5/1989 | George et al. |

(Continued)

FOREIGN PATENT DOCUMENTS

EP   0 310 438 A1   4/1989

(Continued)

OTHER PUBLICATIONS

Capron et al, J. Lightwave Tech., vol. 11 No. 12 pp. 2009-2014 (Dec. 1993).

(Continued)

*Primary Examiner*—Frank G. Font
*Assistant Examiner*—Charlie Peng
(74) *Attorney, Agent, or Firm*—David S. Alavi

(57) ABSTRACT

An optical sensor comprises an optical element having diffractive elements and a sensing region. The diffractive elements are collectively arranged to comprise spectral and spatial transformation information and to transform an input optical signal into an output optical signal according to the transformation information. The sensing region is arranged for receiving sample material so that the optical signals spatially overlap the sample material in the sensing region. The diffractive element set and the sensing region are arranged so that the spectral or spatial transformation information varies according to an optical property of the sample material. A sensing method comprises: receiving into the sensing region the sample material; receiving into the optical element the input optical signal; and receiving from the optical element the output optical signal. The method may further comprise measuring the variation of the spectral transformation information resulting from the sample substance.

51 Claims, 12 Drawing Sheets

U.S. PATENT DOCUMENTS

| | | | |
|---|---|---|---|
| 4,846,552 A | 7/1989 | Veldkamp et al. | |
| 4,923,271 A | 5/1990 | Henry et al. | |
| 4,938,553 A | 7/1990 | Maerz et al. | |
| 5,040,864 A | 8/1991 | Hong | |
| 5,107,359 A | 4/1992 | Ohuchida | |
| 5,165,104 A | 11/1992 | Weverka | |
| 5,195,161 A | 3/1993 | Adar et al. | |
| 5,357,591 A | 10/1994 | Jiang et al. | |
| 5,450,511 A | 9/1995 | Dragone | |
| 5,455,178 A * | 10/1995 | Fattinger | 436/164 |
| 5,738,825 A * | 4/1998 | Rudigier et al. | 422/82.11 |
| 5,768,450 A | 6/1998 | Bhagavatula | |
| 5,812,318 A | 9/1998 | Babbitt et al. | |
| 5,822,472 A * | 10/1998 | Danielzik et al. | 385/12 |
| 5,830,622 A | 11/1998 | Canning et al. | |
| 5,864,641 A * | 1/1999 | Murphy et al. | 385/12 |
| 6,011,884 A | 1/2000 | Dueck et al. | |
| 6,011,885 A | 1/2000 | Dempewolf et al. | |
| 6,137,933 A | 10/2000 | Hunter et al. | |
| 6,144,480 A | 11/2000 | Li et al. | |
| 6,169,613 B1 | 1/2001 | Amitai et al. | |
| 6,169,614 B1 | 1/2001 | Whitcomb et al. | |
| 6,285,813 B1 | 9/2001 | Schultz et al. | |
| 6,323,970 B1 | 11/2001 | Popovich | |
| 6,473,232 B2 | 10/2002 | Ogawa | |
| 6,553,162 B1 | 4/2003 | Okayama | |
| 6,678,429 B2 | 1/2004 | Mossberg et al. | |
| 6,702,897 B2 | 3/2004 | Cullen et al. | |
| 6,823,115 B2 | 11/2004 | Greiner et al. | |
| 6,829,417 B2 | 12/2004 | Greiner et al. | |
| 6,859,318 B1 | 2/2005 | Mossberg | |
| 6,879,441 B1 | 4/2005 | Mossberg | |
| 6,961,491 B2 | 11/2005 | Greiner et al. | |
| 6,965,464 B2 | 11/2005 | Mossberg | |
| 6,965,716 B2 | 11/2005 | Greiner et al. | |
| 6,985,656 B2 | 1/2006 | Iazikov et al. | |
| 6,987,911 B2 | 1/2006 | Mossberg et al. | |
| 6,990,276 B2 | 1/2006 | Brice et al. | |
| 6,993,217 B2 * | 1/2006 | Maruyama et al. | 385/16 |
| 6,993,223 B2 | 1/2006 | Greiner et al. | |
| 7,009,743 B2 | 3/2006 | Mossberg | |
| 7,054,517 B2 | 5/2006 | Mossberg et al. | |
| 7,167,615 B1 * | 1/2007 | Wawro et al. | 385/37 |
| 2003/0039444 A1 | 2/2003 | Mossberg et al. | |
| 2003/0117677 A1 | 6/2003 | Mossberg | |
| 2004/0076374 A1 | 4/2004 | Greiner et al. | |
| 2004/0131360 A1 | 7/2004 | Iazikov et al. | |
| 2004/0170356 A1 | 9/2004 | Iazikov et al. | |
| 2004/0173680 A1 * | 9/2004 | Mossberg et al. | 235/454 |
| 2004/0179779 A1 | 9/2004 | Greiner et al. | |
| 2004/0208466 A1 | 10/2004 | Mossberg et al. | |
| 2004/0258356 A1 | 12/2004 | Brice et al. | |
| 2005/0018951 A1 | 1/2005 | Mossberg et al. | |
| 2005/0078912 A1 | 4/2005 | Iazikov et al. | |
| 2005/0135723 A1 * | 6/2005 | Carr et al. | 385/12 |
| 2005/0135744 A1 | 6/2005 | Greiner et al. | |
| 2005/0135745 A1 | 6/2005 | Greiner et al. | |
| 2005/0135747 A1 | 6/2005 | Greiner et al. | |
| 2005/0152011 A1 | 7/2005 | Mossberg | |
| 2005/0163425 A1 | 7/2005 | Greiner et al. | |
| 2005/0213868 A1 * | 9/2005 | Cunningham | 385/12 |
| 2006/0023280 A1 | 2/2006 | Mossberg | |

FOREIGN PATENT DOCUMENTS

| | | |
|---|---|---|
| GB | 2 168 215 A | 6/1986 |
| WO | WO-99/35523 A1 | 7/1999 |
| WO | WO-99/56159 A1 | 11/1999 |
| WO | WO 02-075411 | 9/2002 |

OTHER PUBLICATIONS

Deri et al, IEEE Photonics Tech. Lett., vol. 6 No. 2 pp. 242-244 (Feb. 1994).

Grunnet-Jepsen et al, Electon. Lett., vol. 35 No. 13 pp. 1096-1097 (Jun. 1999).

Paddon et al, Opt. Lett., vol. 23 No. 19 pp. 1529-1531 (1998).

Madsen et al, IEEE J. Sel. Top. Quant. Elec., vol. 4 No. 6 pp. 925-929 (Nov./Dec. 1998).

Gini et al, J. Lightwave Tech., vol. 16 No. 4 pp. 625-630 (Apr. 1998).

Day et al, J. Lightwave Tech., vol. 14 No. 8 pp. 1815-1824 (Aug. 1996).

McGreer, IEEE Photonics Tech. Lett., vol. 7 No. 3 pp. 324-326 (Mar. 1995).

Takenouchi et al, Optics Express, vol. 6 No. 6 pp. 124-135 (Mar. 2000).

Grunnett-Jepsen et al, Photonics Tech. Lett., vol. 11 No. 10 p. 1283 (Oct. 1999).

Babbitt et al, Opt. Commun., vol. 148 pp. 23-26 (1998).

Brigham et al, Analysis of scattering from large planar gratings of compliant ctlindrical shells, J. Acoust. Soc. Am., vol. 61 No. 1 pp. 48-59 (Jan. 1977).

Kurokawa et al, Electron. Lett., vol. 33 No. 22 pp. 1890-1891 (Oct. 1997).

Sudho et al, J. Lightwave Tech., vol. 8 No. 6 pp. 998-1006 (Jun. 1990).

Henry, J. Lightwave Tech., vol. 8 No. 5 pp. 748-755 (May 1990).

Koontz et al, Appl. Phys. Lett., vol. 71 No. 10 pp. 1400-1402 (Sep. 1997).

Song et al, Appl. Opt., vol. 34 No. 26 pp. 5913-5919 (Sep. 1995).

Brazas et al, Appl. Opt., vol. 34 No. 19 pp. 3786-3792 (Jul. 1995).

Bates et al, Appl. Opt., vol. 32 No. 12 pp. 2112-2116 (Apr. 1993).

Wang et al, Appl. Opt., vol. 32 No. 14 pp. 2606-2613 (May 1993).

Magnusson et al, Appl. Phys. Lett., vol. 61 No. 9 pp. 1022-1024 (Aug. 1992).

Ojha et al, Demonstration of low loss integrated InGaAsP/InP demultiplexer device with low polarisation sensitivity, Electron. Lett., vol. 29 No. 9 p. 805 (Apr. 1993).

Li, Opt. Commum., vol. 114 pp. 406-412 (1995).

Soole et al, Electron. Lett., vol. 31 No. 15 pp. 1276-1277 (Jul. 1995).

Rantala et al, Electron. Lett. vol. 34 No. 5 pp. 455-456 (Mar. 1998).

Cowin et al Electron. Lett., vol. 35 No. 13 pp. 1074-1076 (Jun. 1999).

Canning et al, Opt. Commun., vol. 171 pp. 213-217 (1999).

Tien et al, Use of concentric-arc grating as a thin-film spectrograph for guided waves, Am. Inst. of Physics (1980) pp. 524-525.

Kaneko et al, IEEE J. Sel. Top. Quant. Elec., vol. 5 No. 5 pp. 1227-1236 (Sep./Oct. 1999).

Sun et al, IEEE Photonics Tech. Lett., vol. 10 No. 1 pp. 90-92 (Jan. 1998).

McGreer, IEEE Photonics Tech. Lett., vol. 8 No. 4 pp. 551-553 (Apr. 1996).

Avrutsky et al, IEEE Photonics Tech. Lett., vol. 10 No. 6 pp. 839-841 (1998).

Alavie at al, IEEE Photonics Tech. Lett., vol. 5 No. 9 pp. 1112-1114 (Sep. 1993).

Fu et al, Opt. Lett., vol. 22 No. 21 pp. 1627-1629 (1997).

Wang et al, IEEE Photonics Tech. Lett., vol. 3 No. 1 pp. 36-38 (Jan. 1991).

Wang et al Opt. Lett., vol. 15 No. 7 pp. 363-365 (Apr. 1990).

Wu et al, J. Lightwave Tech., vol. 10 No. 11 pp. 1575-1589 (Nov. 1992).

Eldada et al, IEEE Photonics Tech. Lett., vol. 12 No. 7 pp. 819-821 (Jul. 2000).

Chen et al, J. Lightwave Tech., vol. 10 No. 7 pp. 888-897 (Jul. 1992).

Minier et al, Diffraction characateristics of superimposed holographic gratings in planar optical waveguides, IEEE Photonics Tech. Lett., vol. 4 No. 10 p. 1115 (Oct. 1992).

Miya, IEEE J. Sel. Top. Quant. Elec., vol. 6 No. 1 pp. 38-45 (Jan./Feb. 2000).

Backlund et al, IEEE Photonics Tech. Lett., vol. 12 No. 3 pp. 314-316 (Mar. 2000).

Wiesman et al, IEEE Photonics Tech. Lett., vol. 12 No. 6 pp. 639-641 (Jun. 2000).

Ura et al, Integrated optical wavelength demultiplexer using a coplanar grating lens, Appl. Opt., vol. 29 No. 9 pp. 1369-1373 (Mar. 1990).

Chen et al, Ten channel single-mode wavelength division demultiplexer in the near IR, Integrated Optical Circuits, vol. 1583 pp. 134-142 (Intl. Soc. Opt. Eng., Boston, MA, USA, Sep. 1991).

Babbitt et al, Opt. Lett., vol. 20 No. 8 pp. 910-912 (Apr. 1995).

Mossberg, Opt. Lett., vol. 26 No. 7 pp. 414-416 (Apr. 2001).

Tang et al, A novel wavelength-division-demultiplexer with optical in-plane to surface-normal conversion, IEEE Photonics Tech. Lett., vol. 7 No. 8 p. 908 (Aug. 1995).

Brady et al, Applied Optics, vol. 30 No. 17 p. 2324 (Jun. 1991).

Preston, "Digital holographic logic", Pattern Recognition, vol. 5, p. 37 (1973).

Hirayama et al, Applied Physics Letters, vol. 69 No. 6 p. 791 (Aug. 5, 1996).

Lohmann et al, Applied Optics, vol. 34 No. 17 p. 3172 (Jun. 10, 1995).

* cited by examiner

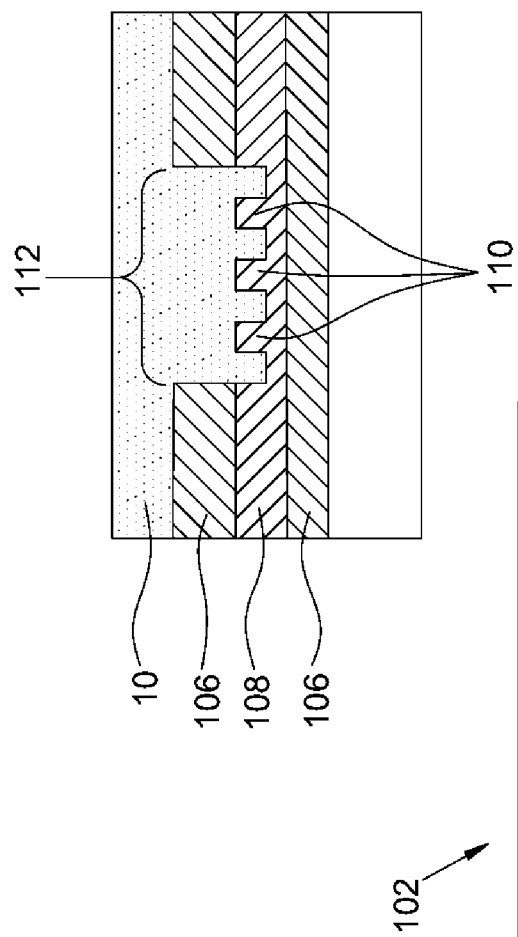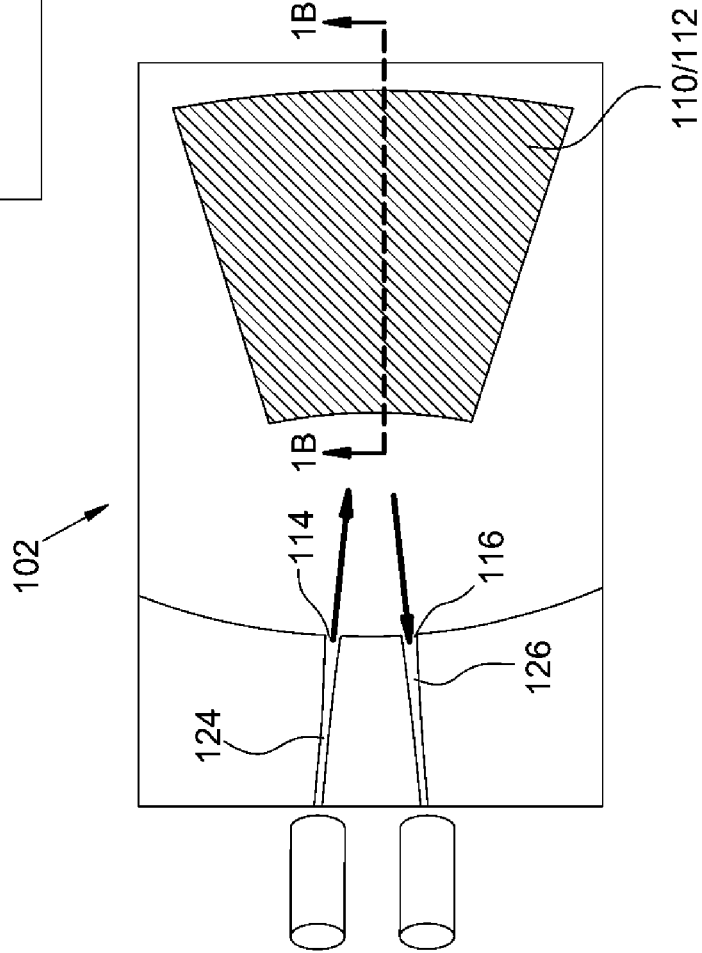

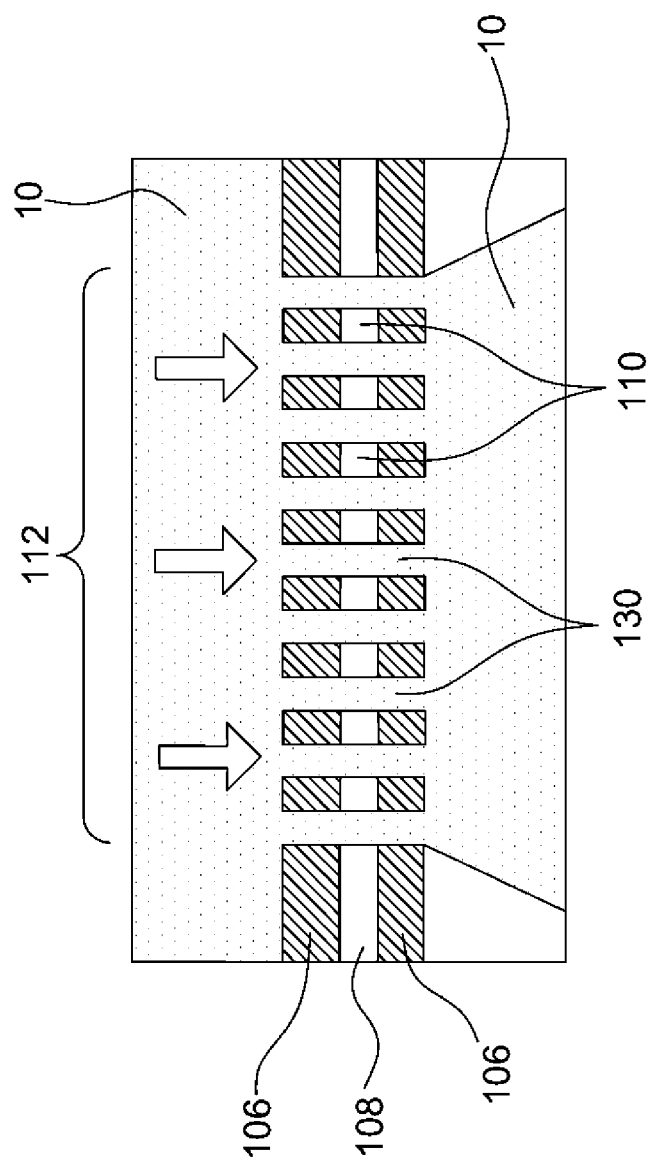
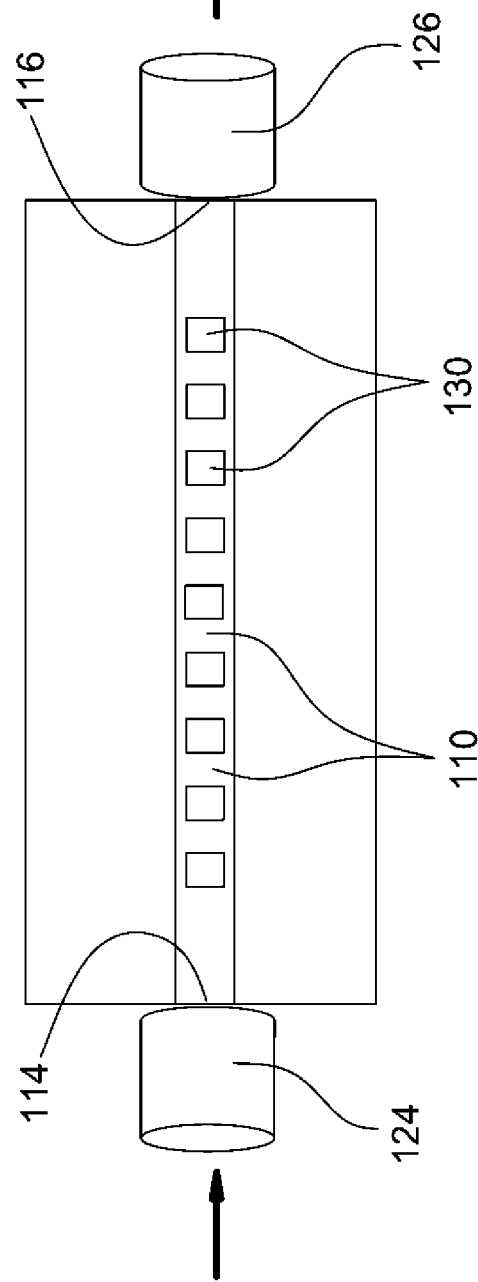
FIG. 3D
FIG. 3A

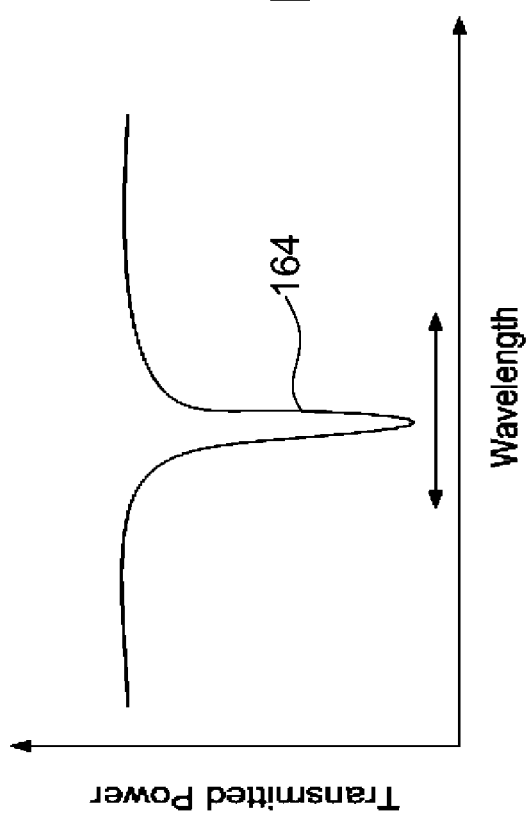
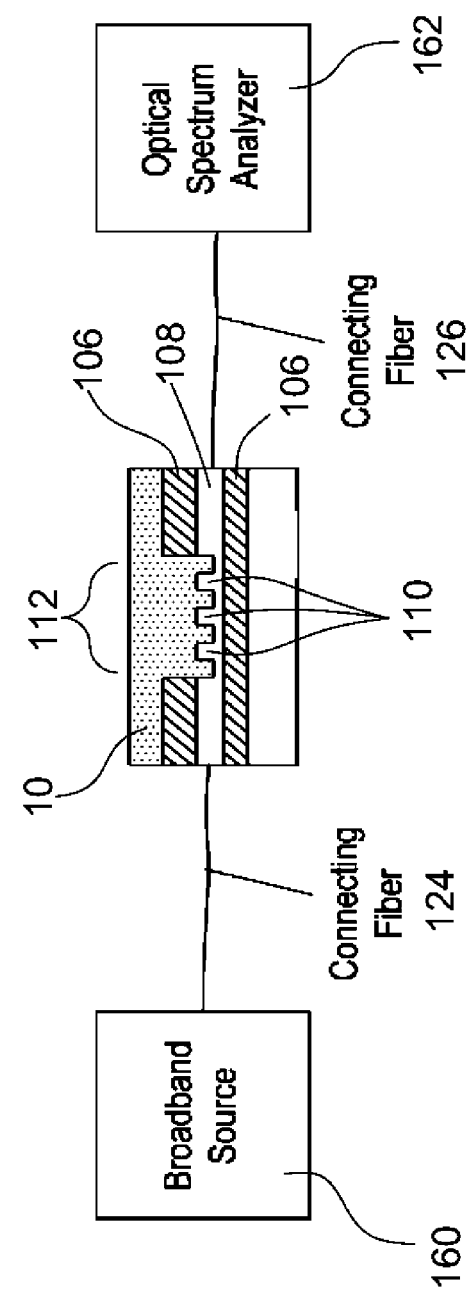
FIG. 6B
FIG. 6A

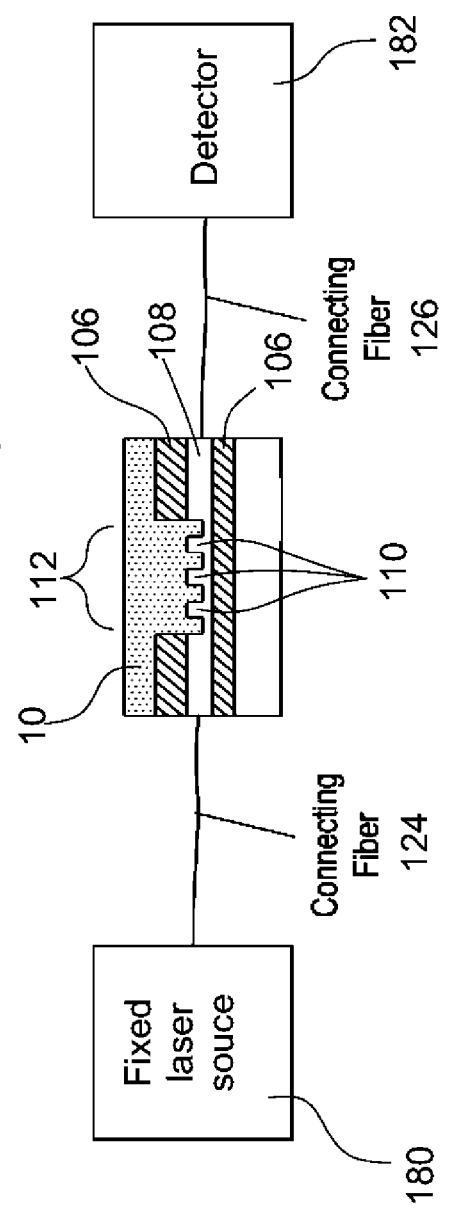
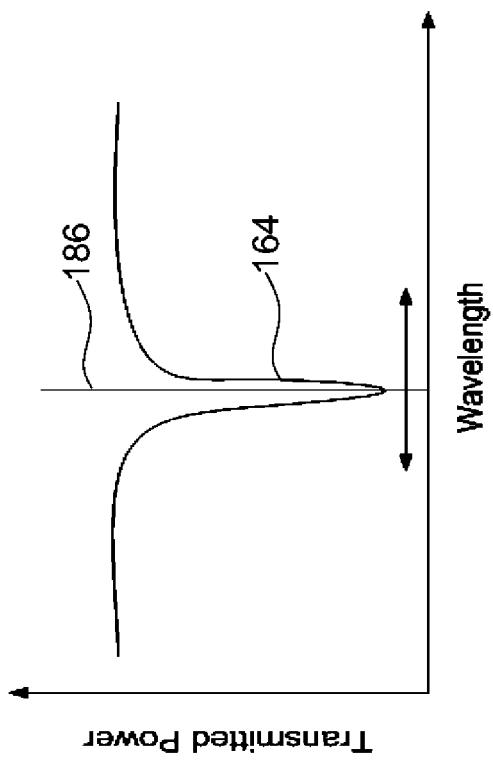
FIG. 8B
FIG. 8A

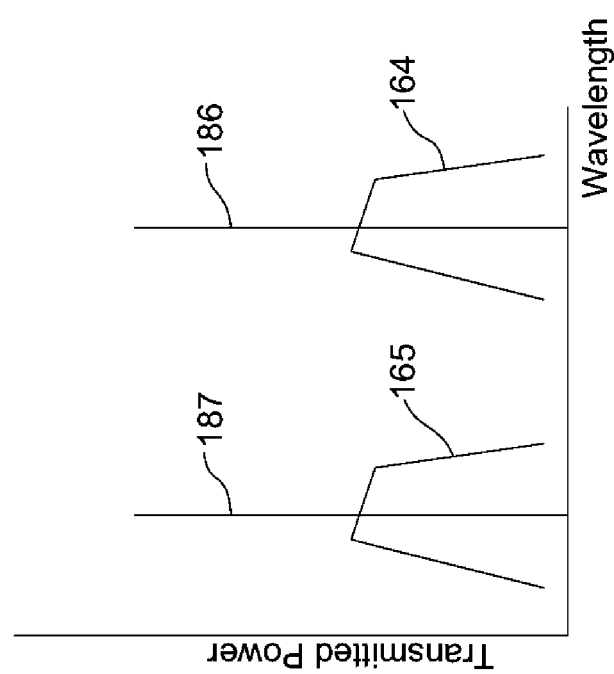
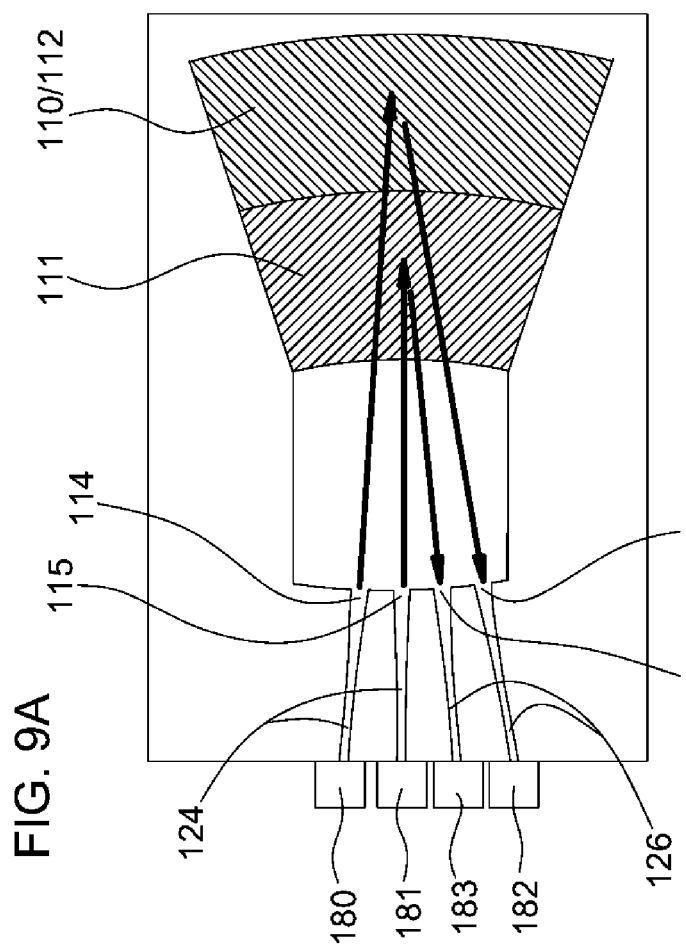
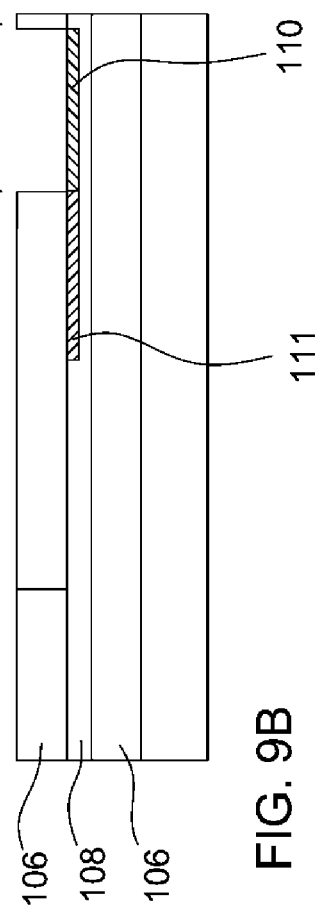

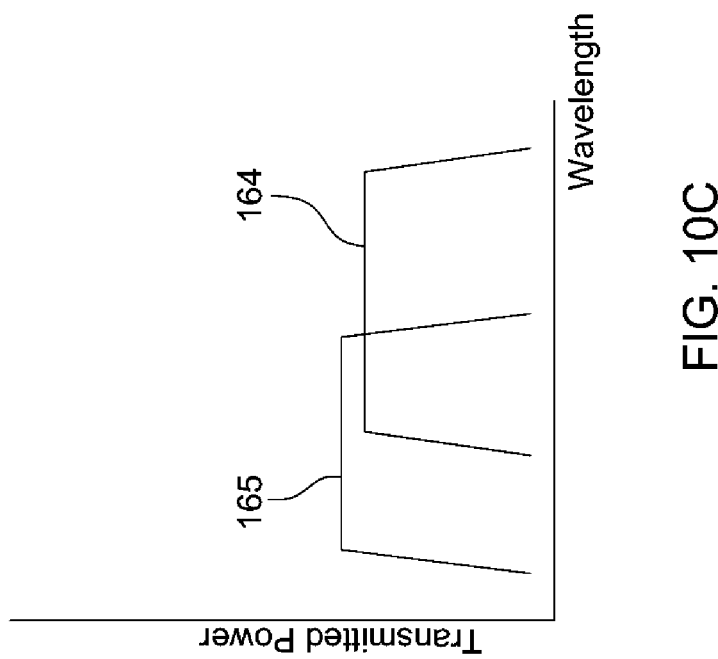
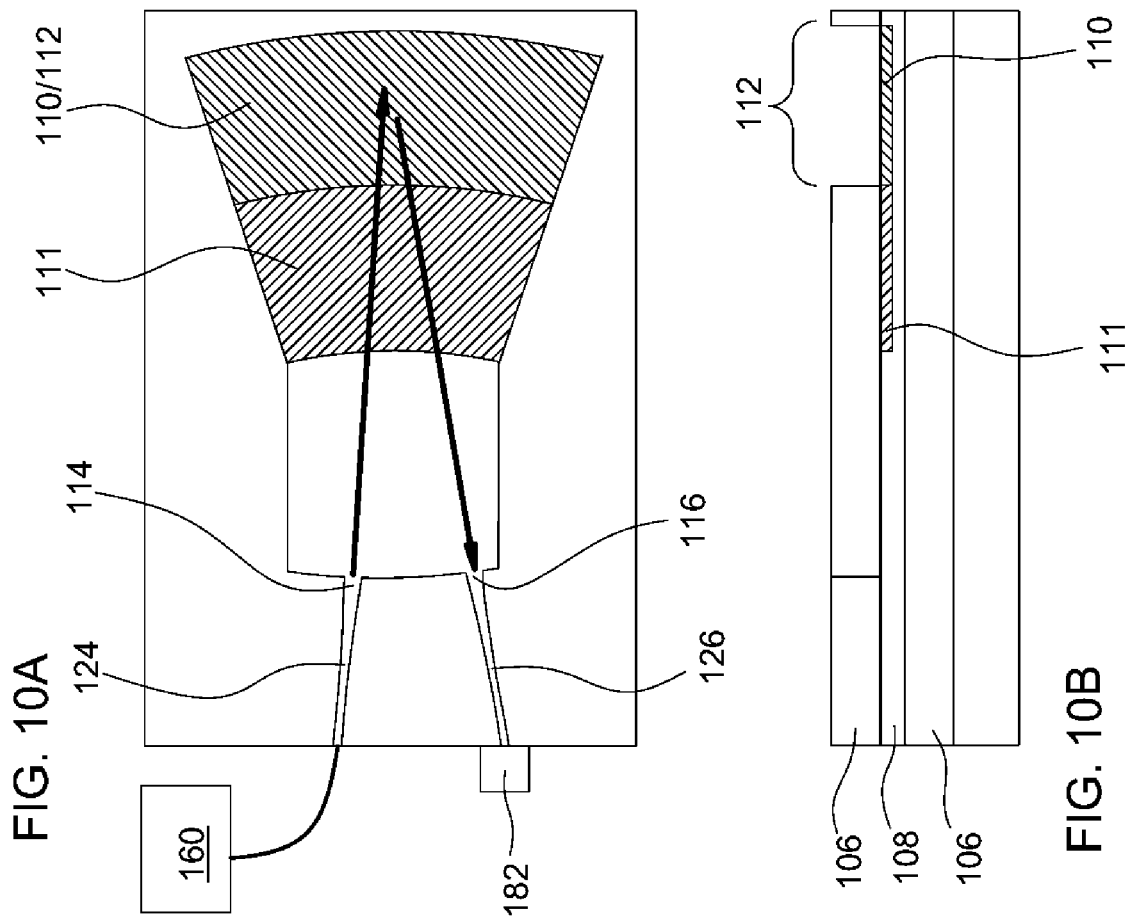
FIG. 10A
FIG. 10B
FIG. 10C

INTEGRATED OPTICAL SENSOR INCORPORATING SETS OF DIFFRACTIVE ELEMENTS

BENEFIT CLAIMS TO RELATED APPLICATIONS

This application claims benefit of prior-filed now abandoned U.S. provisional App. No. 60/659,146 filed Mar. 7, 2005, said provisional application being hereby incorporated by reference as if fully set forth herein.

BACKGROUND

The field of the present invention relates to integrated optical sensors. In particular, disclosed herein are various embodiments of an integrated optical sensor incorporating one or more sets of diffractive elements.

Various embodiments, implementations, and adaptations of optical waveguides with diffractive element sets are disclosed in:

application Ser. No. 11/361,407 filed Feb. 23, 2006 in the name of Thomas W. Mossberg (now U.S. Pat. No. 7,116,453 issued Oct. 3, 2006);

application Ser. No. 11/334,039 filed Jan. 17, 2006 in the names of Thomas W. Mossberg, Christoph M. Greiner, and Dmitri Iazikov;

application Ser. No. 11/298,290 filed Dec. 9, 2005 in the names of Thomas W. Mossberg, Dmitri Iazikov, and Christoph M. Greiner;

application Ser. No. 11/280,876 filed Nov. 15, 2005 in the names of Christoph M. Greiner, Dmitri Iazikov, and Thomas W. Mossberg;

application Ser. No. 11/239,540 filed Sep. 28, 2005 in the name of Thomas W. Mossberg (now U.S. Pat. No. 7,009,743 issued Mar. 7, 2006);

application Ser. No. 11/213,345 filed Aug. 25, 2005 in the names of Christoph M. Greiner, Dmitri Iazikov, and Thomas W. Mossberg (now U.S. Pat. No. 7,120,334 issued Oct. 10, 2006);

application Ser. No. 11/210,439 filed Aug. 23, 2005 in the names of Dmitri Iazikov, Christoph M. Greiner, and Thomas W. Mossberg;

application Ser. No. 11/155,327 filed Jun. 16, 2005 in the names of Christoph M. Greiner, Thomas W. Mossberg, and Dmitri Iazikov (now U.S. Pat. No. 7,190,856 issued Mar. 13, 2007);

application Ser. No. 11/076,251 filed Mar. 8, 2005 in the name of Thomas W. Mossberg (now U.S. Pat. No. 7,062,128 issued Jun. 13, 2006);

application Ser. No. 11/062,109 filed Feb. 17, 2005 in the names of Christoph M. Greiner, Thomas W. Mossberg, and Dmitri Iazikov (now U.S. Pat. No. 7,181,103 issued Feb. 20, 2007);

application Ser. No. 11/055,559 filed Feb. 9, 2005 in the names of Christoph M. Greiner, Thomas W. Mossberg, and Dmitri Iazikov (now U.S. Pat. No. 7,123,794 issued Sep. 17, 2006);

application Ser. No. 11/021,549 filed Dec. 23, 2004 in the names of Dmitri Iazikov, Christoph M. Greiner, and Thomas W. Mossberg;

application Ser. No. 10/998,185 filed Nov. 26, 2004 in the names of Dmitri Iazikov, Christoph M. Greiner, and Thomas W. Mossberg (now U.S. Pat. No. 6,993,223 issued Jan. 31, 2006);

application Ser. No. 10/989,244 filed Nov. 15, 2004 in the names of Christoph M. Greiner, Thomas W. Mossberg, and Dmitri Iazikov (now U.S. Pat. No. 6,961,491 issued Nov. 1, 2005);

application Ser. No. 10/989,236 filed Nov. 15, 2004 in the names of Christoph M. Greiner, Dmitri Iazikov, and Thomas W. Mossberg (now U.S. Pat. No. 6,965,716 issued Nov. 15, 2005);

application Ser. No. 10/923,455 filed Aug. 21, 2004 in the names of Thomas W. Mossberg, Dmitri Iazikov, and Christoph M. Greiner (now U.S. Pat. No. 7,054,517 issued May 30, 2006);

application Ser. No. 10/898,527 filed Jul. 22, 2004 in the named of Dmitri Iazikov, Christoph M. Greiner, and Thomas W. Mossberg (now U.S. Pat. No. 7,194,164 issued Mar. 20, 2007);

application Ser. No. 10/857,987 filed May 29, 2004 in the names of Lawrence D. Brice, Christoph M. Greiner, Thomas W. Mossberg, and Dmitri Iazikov (now U.S. Pat. No. 6,990,276 issued Jan. 24, 2006);

application Ser. No. 10/842,790 filed May 11, 2004 in the names of Thomas W. Mossberg, Christoph M. Greiner, and Dmitri Iazikov (now U.S. Pat. No. 6,987,911 issued Jan. 17, 2006);

application Ser. No. 10/798,089 filed Mar. 10, 2004 in the names of Christoph M. Greiner, Thomas W. Mossberg, and Dmitri Iazikov (now U.S. Pat. No. 6,823,115 issued Nov. 23, 2004);

application Ser. No. 10/794,634 filed Mar. 5, 2004 in the names of Dmitri Iazikov, Thomas W. Mossberg, and Christoph M. Greiner (now U.S. Pat. No. 6,985,656 issued Jan. 10, 2006);

application Ser. No. 10/740,194 filed Dec. 17, 2003 in the names of Dmitri Iazikov, Thomas W. Mossberg, and Christoph M. Greiner (now U.S. Pat. No. 7,224,855 issued May 29, 2007);

application Ser. No. 10/653,876 filed Sep. 2, 2003 in the names of Christoph M. Greiner, Dmitri Iazikov, and Thomas W. Mossberg (now U.S. Pat. No. 6,829,417 issued Dec. 7, 2004);

application Ser. No. 10/602,327 filed Jun. 23, 2003 in the name of Thomas W. Mossberg (now U.S. Pat. No. 6,859,318 issued Feb. 22, 2005);

application Ser. No. 10/229,444 filed Aug. 27, 2002 in the names of Thomas W. Mossberg and Christoph M. Greiner (now U.S. Pat. No. 6,678,429 issued Jan. 13, 2004);

application Ser. No. 09/843,597 filed Apr. 26, 2001 in the name of Thomas W. Mossberg (now U.S. Pat. No. 6,965,464 issued Nov. 11, 2005);

application Ser. No. 09/811,081 filed Mar. 16, 2001 in the name of Thomas W. Mossberg (now U.S. Pat. No. 6,879,441 issued Apr. 12, 2005).

Each of said applications and patents is hereby incorporated by reference as if fully set forth herein. For one or more of the references incorporated hereinabove, it may be the case that the devices, structures, embodiments, implementations, adaptations, procedures, or techniques disclosed therein may be employed, within the scope of the present disclosure or appended claims, for implementing an integrated optical sensor incorporating one or more diffractive element sets.

SUMMARY

An exemplary optical apparatus comprises an optical element having at least one set of diffractive elements and a sensing region. The diffractive elements of the set are collectively arranged so as to comprise spectral and spatial transformation information. The diffractive elements of the set are collectively arranged so as to transform at least a portion of an input optical signal into an output optical signal according to the spectral and spatial transformation information. The input optical signal propagates from an input optical port; the output optical signal propagates to an output optical port. The input optical signal or the output optical signal propagates within the optical element so as to be successively incident on the diffractive elements of the set. The sensing region is arranged for receiving a sample material so that the input optical signal or the output optical signal at least partly spatially overlaps a portion of the sample material in the sensing region. The diffractive element set and the sensing region are arranged so that the spectral or spatial transformation information varies according to at least one optical property of the received sample material.

An optical sensing method comprises: receiving into the sensing region of the optical sensor the sample material; receiving into the optical element via the input optical port the input optical signal; and receiving from the optical element via an output optical port the output optical signal. The method may further comprise measuring the variation of the spectral transformation information resulting from the sample substance.

Objects and advantages pertaining to integrated optical sensors incorporating diffractive element sets may become apparent upon referring to the exemplary embodiments illustrated in the drawings and disclosed in the following written description and/or claims.

BRIEF DESCRIPTION OF THE DRAWINGS

FIGS. 1A-1B are schematic plan and cross-sectional views of an exemplary optical sensor having a diffractive element set.

FIGS. 3A-3C are schematic plan views of an exemplary optical sensors each having a diffractive element set. FIG. 3D is a schematic cross-sectional view of an exemplary optical sensor having a diffractive element set.

FIG. 6A is a schematic cross-sectional view of an exemplary optical sensor having a diffractive element set. FIG. 6B schematically illustrates a spectral feature of the sensor of FIG. 6A.

FIG. 8A is a schematic cross-sectional view of an exemplary optical sensor having a diffractive element set. FIG. 8B schematically illustrates a spectral feature of the sensor of FIG. 8A.

FIGS. 9A-9B are schematic plan and cross-sectional views of an exemplary optical sensor having a diffractive element set. FIG. 9C schematically illustrates a spectral features of the sensor of FIGS. 9A-9B.

FIGS. 10A-10B are schematic plan and cross-sectional views of an exemplary optical sensor having a diffractive element set. FIG. 10C schematically illustrates a spectral features of the sensor of FIGS. 10A-10B.

Figure 2:
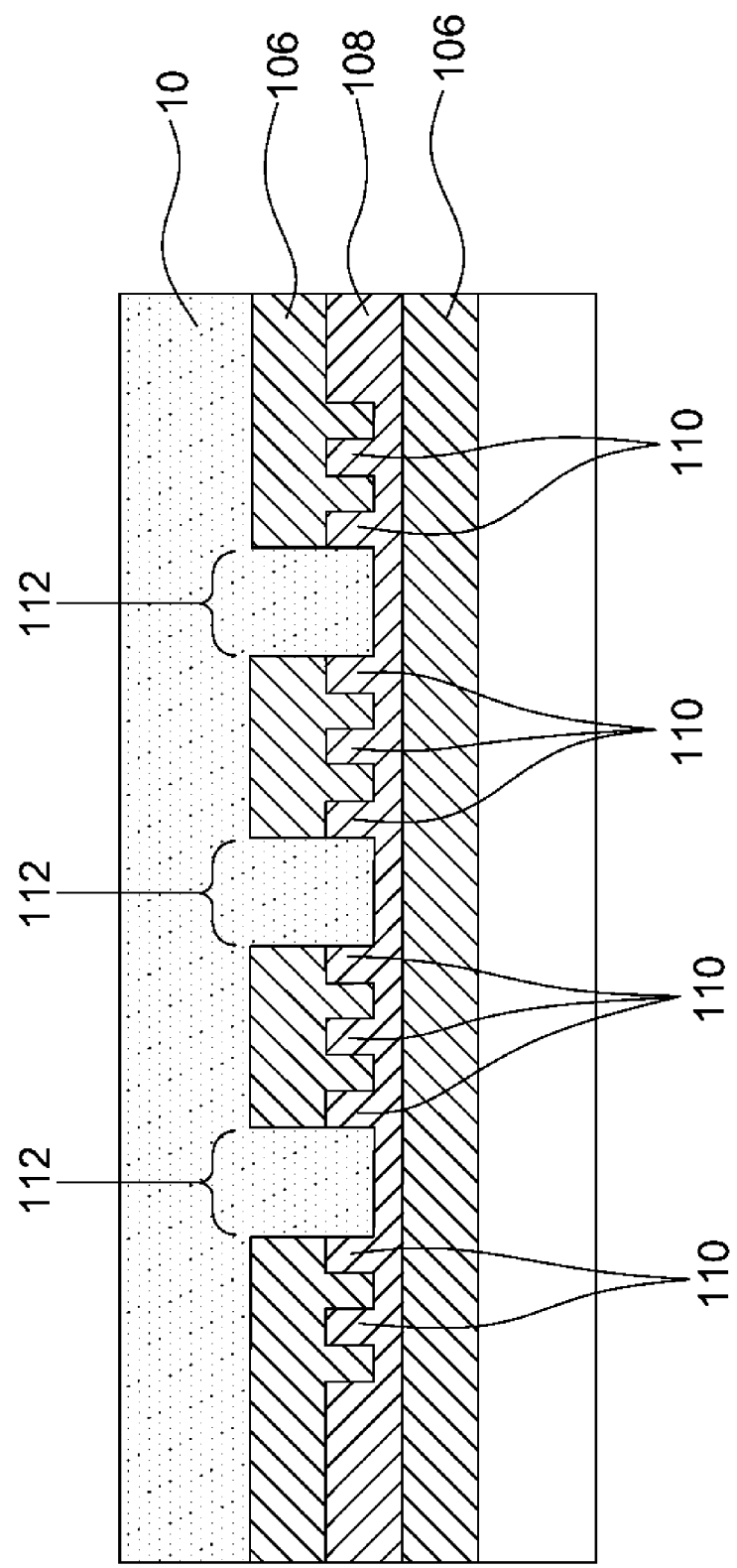
FIG. 2 is a schematic cross-sectional view of an exemplary optical sensor having a diffractive element set.
Figure 3B:
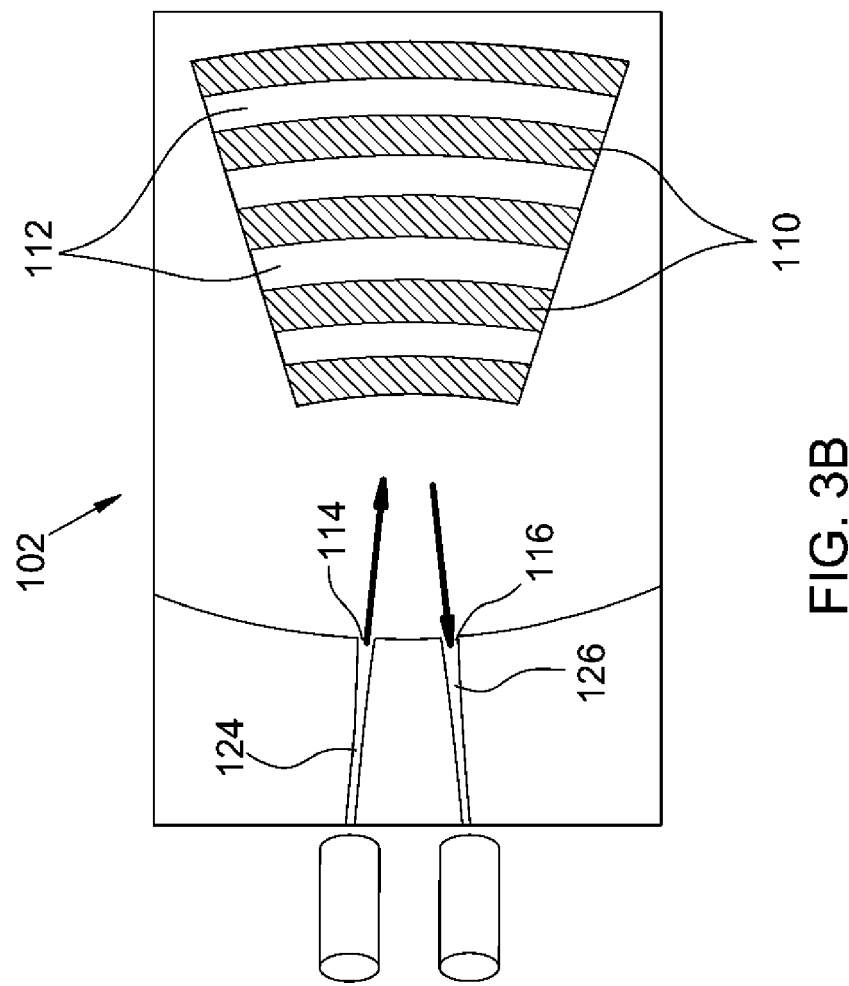
Figure 3C:
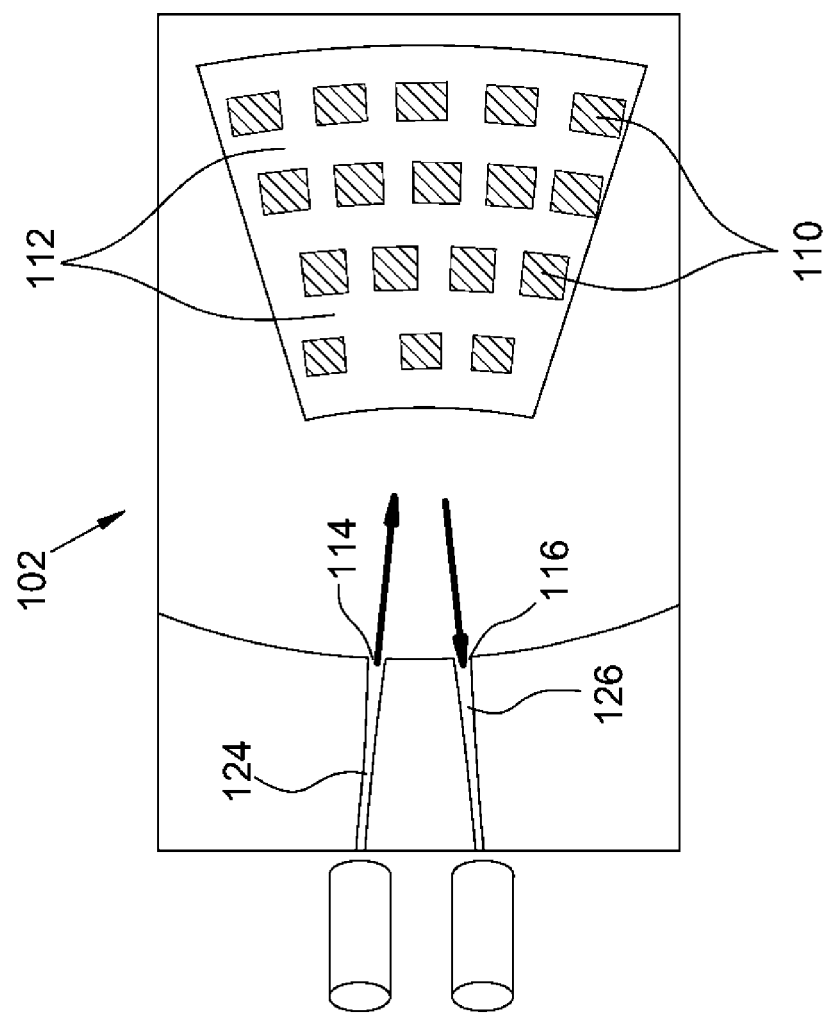

The embodiments shown in the Figures are exemplary, and should not be construed as limiting the scope of the present disclosure and/or appended claims.

DETAILED DESCRIPTION OF EMBODIMENTS

An integrated optical sensor according to the present disclosure comprises an optical element having one or more sets of diffractive elements. The optical element may comprise a planar optical waveguide substantially confining in at least one transverse spatial dimension optical signals propagating therein, or may enable propagation of optical signals in three spatial dimensions therein.

A planar optical waveguide is generally formed on or from a substantially planar substrate of some sort. The confined optical signals typically propagate as transverse optical modes supported or guided by the planar waveguide. These optical modes are particular solutions of the electromagnetic field equations in the space occupied by the waveguide. The planar waveguide may comprise a slab waveguide (substantially confining in one transverse dimension an optical signal propagating in two dimensions therein), or may comprise a channel waveguide (substantially confining in two transverse dimension an optical signal propagating in one dimension therein). It should be noted that the term "planar waveguide" is not used consistently in the literature; for the purposes of the present disclosure and/or appended claims, the term "planar waveguide" is intended to encompass both slab and channel waveguides.

The planar waveguide typically comprises a core surrounded by lower-index cladding (often referred to as upper and lower cladding, or first and second cladding; these may or may not comprise the same materials). The core is fabricated using one or more dielectric materials substantially transparent over a desired operating wavelength range. In some instances one or both claddings may be vacuum, air, or other ambient atmosphere. More typically, one or both claddings comprise layers of dielectric material(s), with the cladding refractive indices $n_1$ and $n_2$ typically being smaller than the core refractive index $n_{core}$. (In some instances in which short optical paths are employed and some degree of optical loss can be tolerated, the cladding indices might be larger than the core index while still enabling the planar waveguide to support guided, albeit lossy, optical modes.) A planar waveguide may support one or more transverse modes, depending on the dimensions and refractive indices of the core and cladding. A wide range of material types may be employed for fabricating a planar waveguide, including but not limited to glasses, polymers, plastics, semiconductors, combinations thereof, and/or functional equivalents thereof. The planar waveguide may be secured to a substrate for facilitating manufacture, for mechanical support, and/or for other reasons. A planar waveguide typically supports or guides one or more optical modes characterized by their respective amplitude variations along the confined dimension.

The set of diffractive elements of the planar optical waveguide may also be referred to as: a set of holographic elements; a volume hologram; a distributed reflective element, distributed reflector, or distributed Bragg reflector (DBR); a Bragg reflective grating (BRG); a holographic Bragg reflector (HBR); a holographic optical processor (HOP); a programmed holographic structure (PHS); a directional photonic-bandgap structure; a mode-selective photonic crystal; or other equivalent terms of art. Each diffractive element of the set may comprise one or more diffracting regions thereof that diffract, reflect, scatter, route, or otherwise redirect portions of an incident optical signal (said process hereinafter simply referred to as diffraction). For a planar waveguide, the diffracting regions of each diffractive element of the set typically comprises some suitable alteration of the planar waveguide (ridge, groove, index modulation, density modulation, and so on), and is spatially defined with respect to a virtual one- or two-dimensional linear or curvilinear diffractive element contour, the curvilinear shape of the contour typically being configured to impart desired spatial characteristics onto the diffracted portion of the optical signal. For an optical element enabling propagation in three dimensions, the virtual diffractive element contour may be an areal contour. Implementation of a diffractive element with respect to its virtual contour may be achieved in a variety of ways, including those disclosed in the references cited hereinabove. Each areal, linear, or curvilinear diffractive element is shaped to direct its diffracted portion of the optical signal to an output optical port, which may be in or out of a plane defined by the diffractive elements. The relative spatial arrangement (e.g. longitudinal spacing) of the diffractive elements of the set, and the relative amplitude diffracted from each diffractive element of the set, yield desired spectral and/or temporal characteristics for the overall diffracted optical signal routed between the corresponding input and output optical ports. It should be noted that optical ports (input and/or output) may be defined structurally (for example, by an aperture, waveguide, fiber, lens, or other optical component) and/or functionally (for example, by a spatial location, convergence/divergence/collimation, and/or propagation direction). For a single-mode planar waveguide, such a set of diffractive elements may be arranged to yield an arbitrary spectral/temporal transfer function (in terms of amplitude and phase). In a multimode planar waveguide, modal dispersion and mode-to-mode coupling of diffracted portions of the optical signal may limit the range of spectral/temporal transfer functions that may be implemented.

The diffractive elements of the set (or equivalently, their corresponding contours) are spatially arranged with respect to one another so that the corresponding portions of the optical signal diffracted by each element interfere with one another at the output optical port, so as to impart desired spectral and/or temporal characteristics onto the portion of the optical signal collectively diffracted from the set of diffractive elements and routed between the input and output optical ports. The diffractive elements in the set are arranged so that an input optical signal, entering the planar waveguide through an input optical port, is successively incident on diffractive elements of the set. For the purposes of the present disclosure and/or appended claims, "successively incident" shall denote a situation wherein a wavevector at a given point on the wavefront of an optical signal (i.e., a wavefront-normal vector; sometimes referred to as a "portion" of the spatial wavefront) traces a path (i.e., a "ray path") through the diffractive element set that successively intersects the virtual contours of diffractive elements of the set. Such wavevectors at different points on the wavefront may intersect a given diffractive element virtual contour at the same time or at differing times; in either case the optical signal is considered "successively incident" on the diffractive elements. A fraction of the incident amplitude is diffracted by a diffractive element and the remainder transmitted and incident on another diffractive element, and so on successively through the set of diffractive elements. The diffractive elements may therefore be regarded as spaced substantially longitudinally along the propagation direction of the incident optical signal, and a given spatial portion of the wavefront of such a successively incident optical signal therefore interacts with many diffractive elements of the set. (In contrast, the diffractive elements of a thin diffraction grating, e.g. the grating lines of a surface grating, may be regarded as spaced substantially transversely across the wavefront of a normally incident optical signal, and a given spatial portion of the wavefront of such a signal therefore interacts with only one or at most a few adjacent diffractive elements).

As described in detail in U.S. non-provisional application Ser. No. 10/998,185 (cited and incorporated by reference hereinabove), diffracting regions of a diffractive element set may be distributed over one of more spatial regions of the optical element, for facilitating placement of multiple diffractive element sets in a single optical element. These spatial regions may be positioned and arranged so as to impart desired spatial, spectral, or temporal characteristics onto the corresponding routed portions of an incident optical signal. Such arrangement may include an optical signal being successively incident on multiple spatial regions of a diffractive element set, with "successively incident" defined as set forth hereinabove. The word "primitive" may be used to designate one diffractive element set among multiple diffractive element sets in a single optical element (e.g., a single optical device may include multiple "primitive programmed holographic structures").

The set of diffractive elements provides dual functionality, spatially routing an optical signal between an input optical port and an output optical port, while at the same time acting to impart a spectral/temporal transfer function onto the diffracted portion of an input optical signal to yield an output optical signal. The diffractive elements may be designed (by computer generation, for example) so as to provide optimal routing, imaging, or focusing of the optical signal between an input optical port and a desired output optical port, thus reducing or minimizing insertion loss. Simple areal, linear, or curvilinear diffractive elements (segments of circles, spheres, ellipses, ellipsoids, parabolas, paraboloids, hyperbolas, hyperboloids, and so forth), if not optimal, may be employed as approximations of fully optimized contours. A wide range of fabrication techniques may be employed for forming the diffractive element set, and any suitable technique(s) may be employed while remaining within the scope of the present disclosure and/or appended claims. Particular attention is called to design and fabrication techniques disclosed in the references cited and incorporated by reference hereinabove. The following are exemplary only, and are not intended to be exhaustive.

Diffractive elements may be formed lithographically on the surface of a planar optical waveguide, or at one or both interfaces between core and cladding of a planar optical waveguide. Diffractive elements may be formed lithographically in the interior of the core layer and/or a cladding layer of the planar optical waveguide using one or more spatial lithography steps performed after an initial partial deposition of layer material. Diffractive elements may be formed in the core and/or cladding layers by projecting ultraviolet light or other suitable radiation through an amplitude and/or phase mask so as to create an interference pattern within the planar waveguide (fabricated at least in part with suitably sensitive material) whose fringe contours match the desired diffractive element contours. Alteration of the refractive index by exposure to ultraviolet or other radiation results in index-modulated diffractive elements. The mask may be zeroth-order-suppressed according to methods known in the art, including the arts associated with fabrication of fiber Bragg gratings. The amplitude and/or phase mask may be produced lithographically via laser writer or e-beam, it may be interferometrically formed, or it may be formed by any other suitable technique. In instances where resolution is insufficient to produce a mask having required feature sizes, a larger scale mask may be produced and reduced to needed dimensions via photoreduction lithography, as in a stepper, to produce a mask at the needed scale. Diffractive elements may be formed by molding, stamping, impressing, embossing, or other mechanical processes. A phase mask may be stamped onto the core or cladding surface followed by optical exposure to create diffractive elements throughout the core and or cladding region. The optical or UV source used to write the diffractive elements in this case should have a coherence length comparable or longer than the distance from the stamped phase mask to the bottom of the core region. Stamping of the phase mask directly on the device may simplify alignment of diffractive elements with ports or other device components especially when those components may be formed in the same or another stamping process. Many approaches to the creation of refractive index modulations or gratings are known in the art and may be employed in the fabrication of diffractive element sets.

Irradiation-produced refractive index modulations or variations for forming diffractive elements will optimally fall in a range between about $10^{-4}$ and about $10^{-1}$; however, refractive index modulations or variations outside this range may be employed as well. Refractive index modulations or variations may be introduced by light of any wavelength (including ultraviolet light) that produces the desired refractive index changes, provided only that the photosensitive material employed is suitably stable in the presence of light in the desired operating wavelength range of the spectral filter. Exposure of a complete set of diffractive elements to substantially spatially uniform, refractive-index-changing light may be employed to tune the operative wavelength range of the diffractive element set. Exposure of the diffractive element set to spatially non-uniform refractive-index changing light may be employed to chirp or otherwise wavelength-modulate the spectral filter (described further hereinbelow). The sensitivity of planar waveguide materials to irradiation produced refractive index modulations may be increased using hydrogen-loading, flame-brushing, boron or other chemical doping, or other method known in the art, for example in the context of making fiber Bragg gratings.

The curvilinear shape of the diffractive element contours may be determined by a variety of standard optical imaging system design tools. Essentially, each diffractive element contour may be optimized to image the input port onto the output port in a phase coherent manner. In some instances, interference among signals diffracted by multiple diffractive elements may contribute to image formation; this may be the case particularly when the diffracted signals propagate out of a plane defined by the diffractive elements. Inputs to the design are the detailed structure of the input and output optical ports and their locations. Standard ray tracing approaches to optical element design may provide a diffractive contour at each optical distance into the planar waveguide that will provide an optimal imaging of the input signal at the input port onto the optimal output signal at the output port. Simple curves may be employed as approximations of the fully optimized contours. Diffractive element virtual contours may be spaced by an optical path difference (as described above) that provides for the field image of successive diffractive contours to be substantially in phase at a desired wavelength. If the overall response of the diffractive element set is to be apodized with amplitude and/or phase modulation (to yield a desired spectral transfer function or impulse response function), the optical spacing of successive diffractive element contours may be controlled to provide required phase differences between diffracted components at the output port, and/or the diffractive strength of the elements may be individually controlled as well (as described in detail in the references cited hereinabove; also described for certain cases in: T. W. Mossberg, "Planar holographic optical processing devices", *Optics Letters* v26 p 414 (2001), said publication being hereby incorporated by reference as if fully set forth herein).

An alternative approach to designing the diffractive element contours for a diffractive element set is to calculate interference patterns between simulated fields at a desired wavelength and with desired waveforms entering the input port and exiting the output port. In forming or writing a summed pattern for the diffractive element set, suitable discretization is applied as needed for any lithographic or UV exposure approach that is utilized for fabrication. The holographic structure may be designed by interference of computer-generated beams having the desired computer-generated temporal waveforms, with the resulting calculated arrangement of diffractive elements implemented by lithography and/or other suitable spatially-selective fabrication techniques. For example, interference between a delta-function-like pulse and a desired reference optical waveform (or its time-reverse) may be calculated, and the resulting interference pattern used to fabricate a diffractive element set that acts to either recognize or generate the desired reference optical waveform.

In an alternative method for making the diffractive element structure, the optical element may include material of appropriate index that is also photosensitive at the wavelength of the desired operational signal beams. As in traditional holography, the input and output recording beams (same wavelength as operational signal beams of the envisioned device) are overlapped in the optical element and the interference pattern between them is recorded. Subsequently the photosensitive material is developed and, if necessary, a cladding may be deposited or attached by other means.

As mentioned in above-cited U.S. Pat. Nos. 6,879,441 and 6,859,318 and U.S. application Ser. No. 11/076,251, inter alia, a single optical apparatus may have multiple primitive sets of diffractive elements. These primitive diffractive element sets may occupy spatial regions in an optical element that are the same, are partially overlapping, or are substantially non-overlapping. More specifically, multiple primitive diffractive element sets may be: i) "stacked" (i.e., positioned one after another along an optical propagation direction from an input port of the optical element); ii) "interleaved" (i.e., the optical element has spatial regions containing diffracting regions of one primitive diffractive element set but no diffracting regions of another primitive diffractive element set; the various spatial regions containing the diffracting regions of a primitive diffractive element set may not be contiguous, but are coherent; the spatial regions may border on other spatial regions containing diffracting regions of other primitive diffractive element sets); iii) overlaid (i.e., the diffracting regions of multiple primitive diffractive element sets occupy a common spatial region); or iv) combined in a common optical element using a combination of these methods. It may be desirable to combine multiple primitive diffractive element sets to create an optical apparatus with multiple outputs and/or inputs, to more efficiently utilize device area, or to meet specific design requirements.

Overlaid primitive diffractive element sets are described in above-cited U.S. Pat. Nos. 6,678,429, 6,829,417, and 6,965,716 and U.S. application Ser. No. 11/280,876. If the fill-factors of diffracting regions of the diffractive elements are sufficiently low (upon implementation of partial-fill grayscale or other apodization technique, for example, as described in the preceding references), then multiple primitive diffractive element sets may be formed in a common spatial region of an optical element with a low probability that diffracting regions of different primitive diffractive element sets would spatially overlap. Such overlap that would occur may be inconsequential, or may be eliminated to any desired degree by element-by-element movement of individual diffracting regions, if desired. At higher fill-factors, a more deterministic approach may be employed for ensuring that diffracting regions for the respective diffractive element sets do not spatially coincide. Depending on the fabrication technique, such considerations may not be necessary. For fabrication by binary lithography, two diffracting regions cannot overlap and function properly. A particular location of the optical element is either etched or not; an optical signal interacts at that location in the same way whether the location was etched to form a single diffracting region or multiple diffracting regions. Fabrication techniques wherein a material response is substantially linear, such as forming diffracting regions by photo-exposure or grayscale lithography, enable formation of diffracting regions that may spatially overlap while each properly fulfills its function. As long as the material response (to the fabrication technique) is substantially linear, a particular location of the optical element will interact differently with an optical signal according to whether it was exposed to form one diffracting regions, two diffracting regions, and so on. For such linear (i.e., grayscale) fabrication techniques, diffractive element sets may be overlaid without regard for fill factor.

Interleaving of multiple primitive diffractive element sets refers to individual primitive diffractive element sets that occupy inter-mixed but substantially non-overlapping spatial regions of an optical element, and is described extensively in above-cited U.S. Pat. No. 6,993,223. Interleaving may be used along with or without other variations of implementing diffracting regions of the diffractive elements (including partial-fill, width-based, line-density, facet-displacement, and element-displacement grayscale methods, other apodization techniques, and so forth). Multiple spatial regions for each of the primitive diffractive element sets may be thought of as forming a "patchwork" over the optical element. Stacking of primitive diffractive element sets might be regarded as the simplest example of interleaving (for which the descriptor "interleaving" may not necessarily even be appropriate), with each primitive diffractive element set occupying a single distinct spatial region of the optical element, and with the spatial regions arranged sequentially along a propagation direction of optical signals (i.e., "stacked"). An incident optical signal is successively incident on each spatial region, and therefore also on each primitive diffractive element set.

True interleaving (i.e., not stacking) may enable improved spectral resolution compared to an optical device of the same overall length with stacked primitive diffractive element sets. It should be noted that in the low to moderate reflection strength case, the spectral resolution $\Delta f_{res}$ (the spectral width of the main reflection maximum) of an unapodized primitive diffractive element set is inversely proportional to the maximal optical path length difference between interfering light beams diffracted by the various diffractive elements of the primitive set. If N primitive programmed holographic structures are stacked and occupy substantially equal portions of a total device length L, the resolution of each primitive diffractive element set is limited by the length L/N. If, on the other hand, N primitive diffractive element sets are each divided into multiple spatial regions, and the spatial regions interleaved so that regions of each primitive set are distributed along the entire length L of the optical element, then the resolution of each primitive diffractive element set would be limited by L. Spatial regions of each primitive diffractive element set may or may not extend across the entire transverse extent of the interleaved multiple diffractive element sets. It is assumed that the various spatial regions of the primitive diffractive element sets are coherent except for phase shifts introduced as part of an overall apodization.

Various adaptation are disclosed and/or claimed in above-cited U.S. Pat. No. 6,993,223 for reducing, minimizing, or substantially eliminating unwanted spatial or spectral characteristics from routed portions of an incident optical signal that may arise due to interleaving of multiple primitive diffractive element sets. These may be achieved by positioning and arranging the spatial regions occupied the primitive diffractive element sets or by control over the refractive index of the optical element as a function of position.

In the following discussion, the depth direction (i.e., propagation direction of an incident optical signal) refers to the direction normal to the phase front of the input beam, while the transverse direction refers to the direction along the phase front of the input beam (perpendicular to the input beam propagation direction). Note that these direction are defined locally for each portion of the spatial wavefront, which is generally curved.

As shown schematically in FIGS. 1A and 1B, an optical apparatus comprises an optical element 102 having at least one set of diffractive elements 110 and a sensing region 112. The diffractive elements 110 of the set are collectively arranged so as to comprise spectral and spatial transformation information. The diffractive elements 110 of the set are collectively arranged so as to transform at least a portion of an input optical signal into an output optical signal according to the spectral and spatial transformation information. The input optical signal propagates from an input optical port 114; the output optical signal propagates to an output optical port 116. The input optical signal or the output optical signal propagating within the optical element so as to be successively incident on the diffractive elements 110 of the set. The sensing region 112 is arranged for receiving a sample material 10 so that the input optical signal or the output optical signal at least partly spatially overlaps a portion of the sample material 10 in the sensing region 112. The diffractive elements 110 of the set and the sensing region 112 are arranged so that the spectral or spatial transformation information varies according to at least one optical property of the received sample material 10.

The set of diffractive elements 110 may be arranged in any suitable way for comprising the spectral and spatial transformation information, including examples disclosed in any of the above-cited references. In an exemplary embodiment, each diffractive element 110 of the set is individually contoured and positioned so as to preferentially route a portion of the input optical signal between the input optical port 114 and the output optical port 116 as the optical signals propagate within the optical element 102. The diffractive elements 110 of each set are collectively arranged so as to exhibit a positional variation in amplitude, optical separation, or spatial phase over some portion of the set. In another exemplary embodiment, each diffractive element 110 of the set diffracts a corresponding diffracted component of the input optical signal with a corresponding diffractive element transfer function between the input optical port 114 and the output optical port 116. Each diffractive element 110 comprises at least one diffracting region having at least one altered optical property so as to enable diffraction of a portion of the input optical signal, and the diffracting regions of each diffractive element 110 are arranged so as to collectively provide the corresponding diffractive element transfer function between the input optical port 114 and the corresponding output optical port 116.

In the exemplary embodiment schematically depicted in FIGS. 1A-1B, the optical element 102 comprises an optical waveguide having a core 108 and cladding 106 substantially confining in at least one transverse dimension the input optical signal or the output optical signal. The sensing region 112 in the embodiment of FIGS. 1A-1B (as well as other exemplary embodiments depicted schematically herein) comprises a region of the optical waveguide having a volume for receiving the sample material 10 in place of at least a portion of the core 108 or the cladding 108, resulting in at least partial spatial overlap of a propagating optical signal with the received sample material 10. Partial spatial overlap of the input optical signal or the output optical signal with the received sample material 10 in the sensor region results in variation of the spectral transformation information of the diffractive elements 110 with variation of an optical property of the received sample material 10. Typically, variation of the index of refraction of the sample material 10 results in corresponding variation in the effective modal index for optical signals propagating in the waveguide. Variation of the modal index in turn results in variation in the spectral characteristics of the output optical signal diffracted by the diffractive elements 110, since the effective optical spacing between diffractive elements varies with the effective modal index. Variation of other optical characteristics of the sample material 110 may also result in variation of the spectral transformation information of the set of diffractive elements 110. For example, wavelength-dependent optical absorption by the sample material may result in altered spatial transformation information for the set of diffractive elements 110. The optical sensor may be used to measure variation in an optical property of the sample material 10, or the measured variation of an optical property may be used to quantitatively or qualitatively characterize another property of the sample material that in turn affects the measured optical property. Sample material properties that may be quantitatively or qualitatively characterized may include but are not limited to: refractive index, optical absorption, density, velocity, pressure, temperature, concentration, composition, and so forth. Any such quantitative or qualitative characterization of the sample material shall fall within the scope of the present disclosure or appended claims.

In the exemplary embodiments schematically depicted in FIGS. 1A, 3B, 3C, 5A, 9, and 10, the optical waveguide comprises a slab waveguide arranged for substantially confining in one transverse dimension optical signals propagating in two dimensions therein. In the exemplary embodiment schematically depicted in FIG. 3A, the optical waveguide comprises a channel waveguide formed on a waveguide substrate and arranged for substantially confining in two transverse dimension optical signals propagating in one dimension therein. The exemplary schematic cross-sectional views of FIGS. 1B, 2, 3D, 4, 5B, 6A, 7A, 8A, 9B, and 10B may each represent either a slab waveguide or a channel waveguide.

An optical sensor may further comprise: an input channel waveguide positioned and adapted for i) receiving the input optical signal, ii) substantially confining the input optical signal in two dimensions as the input optical signal propagates along the input channel waveguide, and iii) transmitting the input optical signal into the optical waveguide at the input optical port; or the optical sensor may further comprise: an output channel waveguide positioned and adapted for i) receiving the output optical signal from the optical waveguide at the output optical port, ii) substantially confining the output optical signal in two dimensions as the output optical signal propagates along the output channel waveguide, and iii) outputting the output optical signal. In the exemplary embodiments schematically depicted in FIGS. 1A, 3B, 3C, 5A, 9A, and 10A, the input channel waveguide(s) 124 and the output optical waveguide(s) 126 each comprise a channel waveguide integrally formed with the optical element 102. In these depicted embodiments, the input and output channel waveguides are variously coupled in turn to optical fibers, optical sources, or optical receivers. In the exemplary embodiments schematically depicted in FIGS. 3A, 6A, 7A, and 8A, the input channel waveguide and output channel waveguide 126 each comprise an optical fiber.

The optical waveguides comprising the optical sensors disclosed herein may be adapted for receiving the input optical signal in only a single transverse optical mode, if needed or desired for satisfying particular operational requirements. Alternatively, the optical sensor may be formed as an optical waveguide adapted for receiving the input optical signal in multiple transverse optical modes. Multimode optical waveguides having diffractive element sets are disclosed in U.S. Pat. No. 6,987,911 and application Ser. No. 11/334,039 cited hereinabove.

The optical waveguide comprising the optical sensors disclosed herein may be arranged for substantially confining both of the input optical signal and the output optical signal. Alternatively, the optical waveguide may be arranged for substantially confining only one of the input optical signal or the output optical signal. The other (i.e. unconfined) optical signal may propagate freely, and may intersect the optical waveguide and the confined optical signal in a region of the optical waveguide occupied by the diffractive element set. In this instance the spatial transformation information includes coupling between the confined and the unconfined optical signals. Such so-called "out-of-plane" optical coupling is disclosed in application Ser. No. 11/055,559 and application Ser. No. 11/062,109 cited hereinabove.

The sensing region 112 of the optical element 102 and the set of diffractive elements 110 may be at least partly stacked, at least partly interleaved, or at least partly overlapped. In the exemplary embodiments schematically depicted in FIGS. 5A-5B, sensing region 112 and multiple sets of diffractive elements 110 are shown stacked. In the exemplary embodiments depicted schematically in FIGS. 2, 3B, and 3C, the sensing region 112 and the set of diffractive elements 110 are interleaved. The adaptations disclosed in U.S. Pat. No. 6,993,223 cited hereinabove may be employed for mitigating effects of the interleaving on spectral or spatial characteristics of the output optical signal(s). In the exemplary embodiments depicted schematically in FIGS. 1A-1B, 3A, 3D, 4, 6A, 7A, 8A, 9A-9B, and 10A-10B, the sensing region 112 and the diffractive elements 110 are overlaid.

Although this need not always be the case, in the exemplary embodiments schematically depicted in the drawings the sensing region 112 is arranged for receiving the sample material 10 in contact with the waveguide core 108, and/or in contact with multiple diffractive elements 110. Bringing the sample material into contact with core 108 increases the spatial overlap of the propagating optical signals with the sample material 10 and therefore increases the sensitivity of the optical sensor to variations in the optical properties of the sample material 10. In embodiments having overlaid sensing region 112 and diffractive elements 110, the sensing region is arranged for receiving the sample material in contact with multiple consecutive diffractive elements 110 of the diffractive element set, as is FIG. 1B, 3D, 4, 6A, 7A, or 8A for example. The spectral transformation information of the set of diffractive elements 110 varies with the refractive index of the sample material 10, for example, since the presence of the sample material 10 determines the effective modal index of the propagating optical signals, which in turn determines the effective optical spacing between the diffractive elements 110. In embodiments having interleaved sensing region 112 and diffractive elements 110, the sensing region 112 and the diffractive elements 110 of the set are arranged for receiving the sample material 10 in spaces between subsets of multiple diffractive elements 110 of the set, as in FIG. 2, 3B, or 3C for example.

In the exemplary embodiment depicted schematically in FIG. 3D, the optical sensor further comprising passages 130 formed through the core 108 in the sensing region 112 for receiving the sample material 10 and for enabling the received sample material 10 to flow through the passages and hence through the waveguide. In other depicted embodiments, the sample material 10 may rest statically in the sensing region 10, or may flow across the sensing region 112 (out of the plane of the cross-sectional views shown in the drawings).

Figure 4:
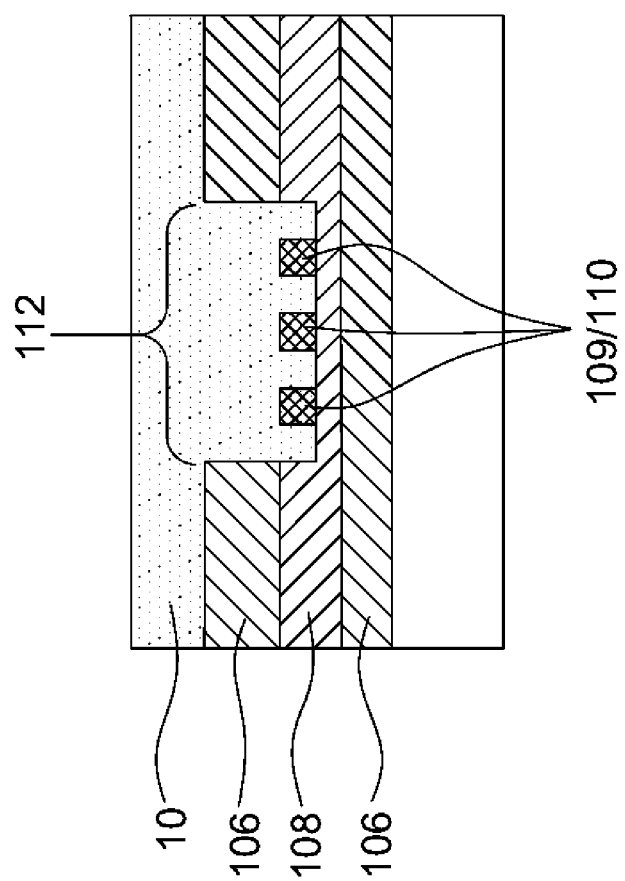
FIG. 4 is a schematic cross-sectional view of an exemplary optical sensor having a diffractive element set.

In the exemplary embodiment depicted schematically in FIG. 4, the optical sensor includes at least one region 109 of the core 108 in contact with the sample material 10 in the sensing region 112 and having a refractive index higher than the refractive index of immediately adjacent regions of the core 108. The sensing region 112 and the higher-index region 109 of the core 108 are arranged for receiving the sample material 10 in contact with the higher-index region 109 and for enhancing spatial overlap of the input optical signal or the output optical signal with the received sample material 10. In the example of FIG. 4, the higher-index region 109 of the core 1089 also includes diffractive elements 110 (i.e., the sensing region 112 and the diffractive elements 110 are overlaid). It could instead be the case that the higher-index region 109 of the core 108 may be interleaved with the diffractive elements 110. In either case the presence of higher-index region 109 of the core 108 enhances spatial overlap of the propagating optical signals with the sample material 10 in the sensor region 112.

The optical sensor may include multiple sets of diffractive elements 110, each arranged so as to comprise corresponding spectral and spatial transformation information and for routing optical signals between corresponding input and output optical ports. The input optical ports may comprise a common input optical port or distinct corresponding input optical ports. Likewise, the output optical ports may comprise a common output optical port or distinct corresponding output optical ports. The multiple diffractive element sets 110 and the sensing region 112 are arranged so that the corresponding spectral or spatial transformation information varies according to at least one optical property of the received sample material 10. The use of multiple diffractive element sets 110 may be advantageous for identification or quantification of multiple selected substances in the sample material 10 that have distinct spectrally-varying properties.

The optical sensor may further comprise a reference set of diffractive elements 111 collectively arranged so as to comprise reference spectral and spatial transformation information and for routing reference optical signals between reference input and output optical ports 115 and 117, respectively, according to the reference spectral and spatial transformation information. The optical element 102 is arranged so that the reference spatial and spectral transformation information is substantially invariant with respect to optical properties of the sample material. This may be readily achieved, as depicted in the exemplary embodiments of FIGS. 7A, 9B, and 10B, by leaving cladding 106 intact in the region of the reference diffractive element set 111, thereby isolating the reference diffractive element set 111 from the sampled substance 10. The presence of a reference diffractive element set 111 enables effects on the optical sensor of temperature, mechanical stress, or other environmental factors to be corrected, since such environmental factors presumably affect both the sensing diffractive element set 110 and the reference diffractive element set 111 in substantially the same way to substantially the same extent. The reference diffractive element set may also, or instead, be used for signal normalization, thereby enabling correction for variations in intensity of an optical source, for example. Any suitable use of the reference diffractive element set shall fall within the scope of the present disclosure or appended claims.

The sensitivity of the optical sensor may be enhanced in several ways. An optical resonator formed in the optical element 102 with at least a portion of the sensing region 112 within the resonator may serve to enhance variation of the spectral and spatial transformation information according to an optical property of the sample material 10. The presence of the resonator amplifies the effect of any change in effective modal index within the resonator due to the presence of the sample material, for example. Alternatively, such a resonator may be employed for cavity ring-down spectroscopy in the optical element 102. The optical sensor may further comprise a receptor material in the sensing region 10 for preferentially binding a selected substance in the sample material 10. Such preferential binding may serve to localize a larger fraction of the selected substance present in the sample material in the sensing region, where its effect on the spectral transformation information is thereby enhanced. Examples of suitable receptor materials may include, but are not limited to, DNA segments, RNA segments, immunoglobulins, antibodies, receptor proteins, other structurally specific biopolymers, ion-exchange resins, self-assembling molecular species, and so forth. Use of a receptor may serve to increase sensitivity or specificity of the optical sensor.

An optical apparatus may include an optical sensor as variously shown and described herein, and may further comprise an optical source for launching the input optical signal into the optical element via the input optical port, and an optical receiver for receiving the output optical signal from the optical element via the output optical port. The optical source may comprise a broadband optical source 160 (FIG. 6A, 7A, or 10A), or may comprise a narrowband optical source 180 or 181 (FIG. 8A or 9A). The terms "broadband" and "narrowband" are used herein for describing the spectral bandwidth of the optical source(s) relative to the spectral width of the spectral transformation information of a diffractive element set. A broadband optical source would have a spectrum wider than spectral features of the transformation information of a diffractive element set, while a narrowband optical source would have a spectrum narrower than spectral features of a diffractive element set. A narrowband optical source operate at a fixed nominal wavelength, or may be tunable. Likewise, a broadband optical source may be tunable, although such sources are more commonly not tunable. Any suitable optical source may be employed, including but not limited to lasers, LEDs, lamps, bulbs, and so on. The receiver may comprise a spectrometer or optical spectrum analyzer 162 (FIG. 6A or 7A), or may comprise a photodetector 182 or 183 (FIG. 8A, 9A, or 10A). It should be noted that a tunable narrowband optical source used in conjunction with a photodetector may serve as a functional equivalent of a broadband optical source used in conjunction with a spectrometer or spectrum analyzer. Both arrangements shall fall within the scope of the present disclosure or appended claims.

Figure 5A:
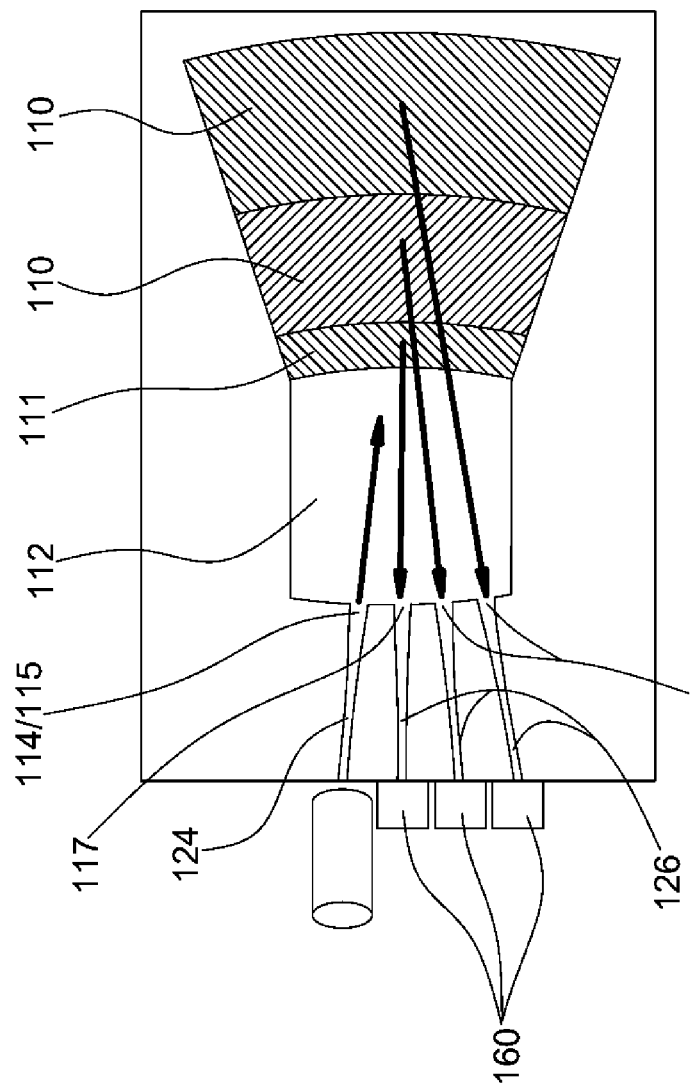
FIGS. 5A-5B are schematic plan and cross-sectional views of an exemplary optical sensor having a diffractive element set.
Figure 5B:
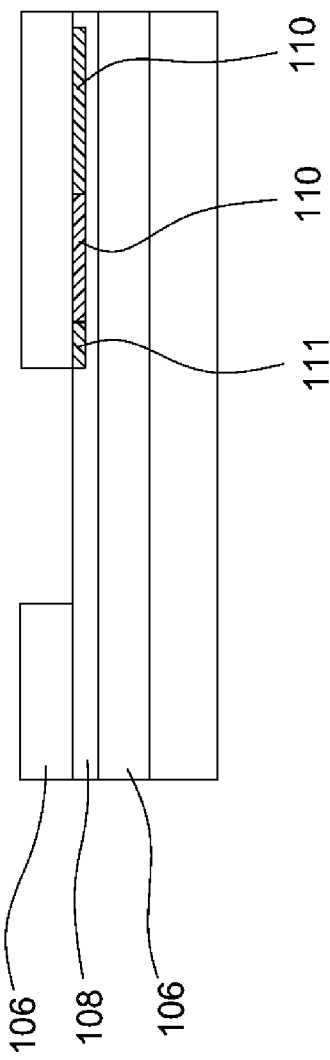

In the exemplary embodiment of FIGS. 5A-5B, the sensing region 112 is distinct from the diffractive element sets 110 and 111. In this example the sensor region enables the sample material 10 to alter the spectral content of broadband optical signals as they propagate through the sensing region 112 without affecting the spectral or spatial transformation information of the diffractive elements 110 or 111. This embodiment may be well suited for measuring relative optical absorption at multiple wavelengths (corresponding to the spectral reflectivity bands of the diffractive element sets 110). The spectral reflectivity band of reference diffractive element set 111 may be shifted away from any absorption of the sample material, and therefore act to provide a normalization signal. Such an arrangement may be used, for example, for determining or estimating relative concentrations of two substances having differing optical absorption spectra.

An optical sensing method comprises: receiving into the sensing region 112 of the optical sensor the sample material 10; receiving into the optical element 102 via the input optical port 114 the input optical signal; and receiving from the optical element via an output optical port 116 the output optical signal. The method may further comprise measuring the variation of the spectral transformation information resulting from the sample substance 10. The method may still further comprise i) analyzing the measured variation of the spectral transformation information to determine presence or absence of a selected substance in the sample material, ii) analyzing the measured variation of the spectral transformation information to quantify a selected substance in the sample material, or iii) analyzing the measured variation of the spectral transformation information to determine one of more properties of sample material 10. Such measurements and analyses may be performed in a wide variety of suitable ways known in the art, and any such suitable techniques, algorithms, methodologies, and so forth shall fall within the scope of the present disclosure or appended claims.

Figure 7B:
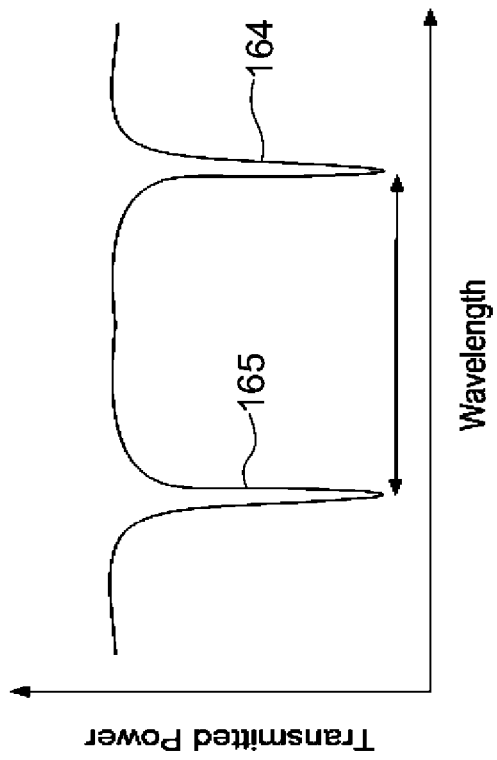
FIG. 7B schematically illustrates spectral features of the sensor of FIG. 7A.
Figure 7A:
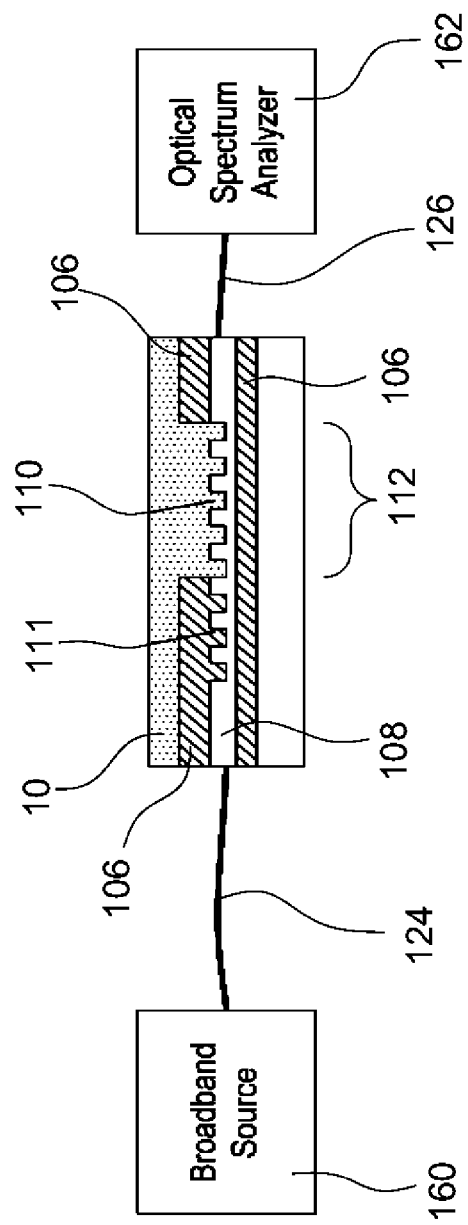
FIG. 7A is a schematic cross-sectional view of an exemplary optical sensor having a diffractive element set.

An optical sensing method may employ a broadband input optical signal, and may further comprise measuring the output optical signal with an optical spectrometer or an optical spectrum analyzer 162 to determine a wavelength of a spectral feature 164 of the output optical signal (FIGS. 6A-6B). Another optical sensing method may employ an optical sensor having a reference diffractive element set 111 and may employ a common broadband optical signal as the input optical signal and as the reference optical signal, and may further comprise measuring the output optical signal and the reference output optical signal with an optical spectrometer or an optical spectrum analyzer 162 to compare a wavelength of a spectral feature 164 of the output optical signal with a wavelength of a spectral feature 165 of the reference output optical signal (FIGS. 7A-7B).

An optical sensing method may employ a narrowband input optical signal, and may further comprise measuring the intensity of the output optical signal with a photodetector 182. Another optical sensing method may employ a narrowband input optical signal and a narrowband reference input optical signal, and may further comprise measuring the intensity of the output optical signal with a signal photodetector 182 and measuring the intensity of the reference output optical signal with a reference photodetector 183. In either case, the intensity measurements may be employed for estimating or determining the wavelength of the spectral feature 164 of the output optical signal relative to the spectral feature 165 of the reference output optical signal, the input optical signal wavelength 186, or the reference input optical signal wavelength 187 (FIG. 8A-8B or 9A-9C). The measured intensity(ies) may be used to determine or estimate the presence/absence of a selected substance in the sample material 10, to quantify the selected substance in the sample material 10, or to determine one or more properties of the sample material 10. In FIGS. 10A-10C, a single broadband source 160 is employed along with a single photodetector 182. The spectral features 164 and 165 of the output and reference optical signals, respectively, partially spectrally overlap. Another optical sensing method may further comprise measuring the sum of the intensities of the output and reference optical signals with photodetector 182, and analyzing the measured intensity to estimate of determine presence, absence, quantity, or condition of the sample material 10 or a selected substance therein.

It should be noted that many of the embodiments depicted in this disclosure are only shown schematically, and that not all the features may be shown in full detail or in proper proportion and/or location. Certain features or structures may be exaggerated relative to others for clarity. In particular, it should be noted that individual diffractive elements are typically not shown; spatial regions having diffracting regions of a particular diffractive element set are shown instead. If individual diffractive elements are shown, typically only a few representative diffractive elements are actually depicted as examples. It should be further noted that the embodiments shown in the Figures are exemplary only, and should not be construed as specifically limiting the scope of the written description or the claims set forth herein. It is intended that equivalents of the disclosed exemplary embodiments and methods shall fall within the scope of the present disclosure or appended claims. It is intended that the disclosed exemplary embodiments and methods, and equivalents thereof, may be modified while remaining within the scope of the present disclosure or appended claims.

For purposes of the present disclosure and appended claims, the conjunction "or" is to be construed inclusively (e.g., "a dog or a cat" would be interpreted as "a dog, or a cat, or both"; e.g., "a dog, a cat, or a mouse" would be interpreted as "a dog, or a cat, or a mouse, or any two, or all three"), unless: i) it is explicitly stated otherwise, e.g., by use of "either . . . or", "only one of . . . ", or similar language; or ii) two or more of the listed alternatives are mutually exclusive within the particular context, in which case "or" would encompass only those combinations involving non-mutually-exclusive alternatives.

What is claimed is:

1. An optical apparatus, comprising an optical element having at least one set of diffractive elements and a sensing region, wherein:
the diffractive elements of the set are collectively arranged so as to comprise spectral and spatial transformation information;
the diffractive elements of the set are collectively arranged so as to transform at least a portion of an input optical signal into an output optical signal according to the spectral and spatial transformation information so that a spatial wavefront of the input optical signal differs from a spatial wavefront of the output optical signal, the input optical signal propagating from an input optical port, the output optical signal propagating to an output optical port, the input optical signal or the output optical signal propagating within the optical element so as to be successively incident on the diffractive elements of the set;
the sensing region is arranged for receiving a sample material so that the input optical signal or the output optical signal at least partly spatially overlaps a portion of the sample material in the sensing region; and
the diffractive element set and the sensing region are arranged so that the spectral or spatial transformation information varies according to at least one optical property of the received sample material.

2. The optical apparatus of claim 1, wherein:
each diffractive element of the set is individually contoured and positioned so as to preferentially route a portion of the input optical signal between the input optical port and the output optical port as the optical signals propagate within the optical element; and
the diffractive elements of each set are collectively arranged so as to exhibit a positional variation in amplitude, optical separation, or spatial phase over some portion of the set.

3. The optical apparatus of claim 1, wherein:
each diffractive element of the set diffracts a corresponding diffracted component of the input optical signal with a corresponding diffractive element transfer function between the input optical port and the corresponding output optical port;
each diffractive element comprises at least one diffracting region having at least one altered optical property so as to enable diffraction of a portion of the input optical signal; and
the diffracting regions of each diffractive element are arranged so as to collectively provide the corresponding diffractive element transfer function between the input optical port and the corresponding output optical port.

4. The apparatus of claim 1, wherein the optical element comprises an optical waveguide having a core and cladding substantially confining in at least one transverse dimension the input optical signal or the output optical signal, and the sensing region comprises a region of the optical waveguide having a volume for receiving the sample material in place of at least a portion of the core or the cladding.

5. The apparatus of claim 4, wherein the optical waveguide comprises a slab waveguide arranged for substantially confining in one transverse dimension optical signals propagating in two dimensions therein, and at least a portion of the slab waveguide spatially overlaps at least a portion of the sensing region or at least a portion of the diffractive element set.

6. The apparatus of claim 4, wherein the optical waveguide comprises a channel waveguide formed on a waveguide substrate and arranged for substantially confining in two transverse dimension optical signals propagating in one dimension therein, and at least a portion of the channel waveguide spatially overlaps at least a portion of the sensing region or at least a portion of the diffractive element set.

7. The apparatus of claim 4, further comprising:
an input channel waveguide positioned and adapted for i) receiving the input optical signal, ii) substantially confining the input optical signal in two dimensions as the input optical signal propagates along the input channel waveguide, and iii) transmitting the input optical signal into the optical waveguide at the input optical port; or
an output channel waveguide positioned and adapted for i) receiving the output optical signal from the optical waveguide at the output optical port, ii) substantially confining the output optical signal in two dimensions as the output optical signal propagates along the output channel waveguide, and iii) outputting the output optical signal.

8. The apparatus of claim 7, wherein the input channel waveguide or the output channel waveguide comprises a channel waveguide integrally formed with the optical waveguide.

9. The apparatus of claim 7, wherein the input channel waveguide or the output channel waveguide comprises an optical fiber.

10. The apparatus of claim 1, wherein the optical waveguide is adapted for receiving the input optical signal in a single transverse optical mode.

11. The apparatus of claim 1, wherein the optical waveguide is adapted for receiving the input optical signal in multiple transverse optical modes.

12. The apparatus of claim 1, wherein the optical waveguide is arranged for substantially confining both of the input optical signal and the output optical signal.

13. The apparatus of claim 1, wherein the optical waveguide is arranged for substantially confining only one of the input optical signal or the output optical signal.

14. The apparatus of claim 1, wherein the sensing region of the optical element and the diffractive element set are at least partly stacked, are at least partly interleaved, or at least partly overlap.

15. The apparatus of claim 1, wherein the optical characteristic is an index of refraction.

16. The apparatus of claim 1, wherein the sensing region is arranged for receiving the sample material in contact with the core.

17. The apparatus of claim 16, wherein the sensing region is arranged for receiving the sample material in contact with multiple diffractive elements of the diffractive element set.

18. The apparatus of claim 17, wherein the sensing region and the diffractive element set are arranged for receiving the sample material in spaces between multiple consecutive diffractive elements of the set.

19. The apparatus of claim 16, wherein the sensing region and the diffractive element set are arranged for receiving the sample material in spaces between subsets of multiple diffractive elements.

20. The apparatus of claim 1, further comprising passages formed through the core for receiving the sample material and for enabling the received sample material to flow therethrough.

21. The apparatus of claim 1, further comprising at least one region of the core in contact with the sample material in the sensing region and having a refractive index higher than the refractive index of immediately adjacent regions of the core, wherein the sensing region and the higher-index region of the core are arranged for receiving the sample material in contact with the higher-index region and for enhancing spatial overlap of the input optical signal or the output optical signal with the received sample material.

22. The apparatus of claim 1, further comprising multiple sets of diffractive elements of the optical element, wherein:
the diffractive elements of each set are collectively arranged so as to comprise corresponding spectral and spatial transformation information;
the diffractive elements of each set are collectively arranged so as to transform at least a portion of an input optical signal into a corresponding output optical signal according to the corresponding spectral and spatial transformation information, the input optical signal propagating from the input optical port, the corresponding output optical signal propagating to a corresponding output optical port, the input optical signal or the corresponding output optical signal propagating within the optical element so as to be successively incident on the diffractive elements of the corresponding set; and
the diffractive element sets and the sensing region are arranged so that the corresponding spectral or spatial transformation information varies according to at least one optical property of the received sample material.

23. The apparatus of claim 1, further comprising:
an optical source for launching the input optical signal into the optical element via the input optical port; and
an optical receiver for receiving the output optical signal from the optical element via the output optical port.

24. The apparatus of claim 23, wherein the optical source comprises a broadband optical source, and the optical receiver comprises an optical spectrometer or an optical spectrum analyzer.

25. The apparatus of claim 23, wherein the optical source comprises a narrowband optical source, and the optical receiver comprises a photodetector.

26. The apparatus of claim 25, wherein the optical source comprises a tunable narrowband optical source, and the optical receiver comprises a photodetector, an optical spectrometer, or an optical spectrum analyzer.

27. The apparatus of claim 1, further comprising a receptor material in the sensing region for preferentially binding a selected substance in the sample material.

28. The apparatus of claim 1, further comprising an optical resonator formed in the optical element with at least a portion of the sensing region within the resonator for enhancing variation of the spectral and spatial transformation information according to the optical property of the sample material.

29. The optical apparatus of claim 1, wherein the diffractive element set and the sensing region are arranged so that the spectral transformation information varies according to at least one optical property of the received sample material and the spatial transformation information is substantially invariant with respect to optical properties of the sample material.

30. The optical apparatus of claim 1, wherein the diffractive element set and the sensing region are arranged so that the spatial transformation information varies according to at least one optical property of the received sample material and the spectral transformation information is substantially invariant with respect to optical properties of the sample material.

31. The optical apparatus of claim 1, wherein the diffractive element set and the sensing region are arranged so that the spectral and spatial transformation information varies according to at least one optical property of the received sample material.

32. A method, comprising:
receiving into a sensing region of an optical element a sample material;
receiving into the optical element via an input optical port an input optical signal, the optical element having at least one set of diffractive elements collectively arranged so as to comprise spectral and spatial transformation information, the diffractive elements of the set being collectively arranged so as to transform at least a portion of the input optical signal into an output optical signal according to the spectral and spatial transformation information so that a spatial wavefront of the input optical signal differs from a spatial wavefront of the output optical signal, the input optical signal or the output optical signal propagating within the optical element so as to be successively incident on the diffractive elements of the set, the sensing region being arranged so that the input optical signal or the output optical signal at least partly spatially overlaps a portion of the sample material in the sensing region, the diffractive element set and the sensing region being arranged so that the spectral or spatial transformation information varies according to at least one optical property of the received sample material; and
receiving from the optical element via an output optical port the output optical signal.

33. The method of claim 32, further comprising measuring variation of the spectral transformation information resulting from the sample substance.

34. The method of claim 33, further comprising analyzing the measured variation of the spectral transformation information to determine presence or absence of a selected substance in the sample material.

35. The method of claim 33, further comprising analyzing the measured variation of the spectral transformation information to quantify a selected substance in the sample material.

36. The method of claim 32, wherein:
each diffractive element of the set is individually contoured and positioned so as to preferentially route a portion of the input optical signal between the input optical port and the output optical port as the optical signals propagate within the optical element; and
the diffractive elements of each set are collectively arranged so as to exhibit a positional variation in amplitude, optical separation, or spatial phase over some portion of the set.

37. The method of claim 32, wherein:
each diffractive element of the set diffracts a corresponding diffracted component of the input optical signal with a corresponding diffractive element transfer function between the input optical port and the corresponding output optical port;
each diffractive element comprises at least one diffracting region having at least one altered optical property so as to enable diffraction of a portion of the input optical signal; and
the diffracting regions of each diffractive element are arranged so as to collectively provide the corresponding diffractive element transfer function between the input optical port and the corresponding output optical port.

38. The method of claim 32, wherein the input optical signal comprises a broadband optical signal, the method further comprising measuring the output optical signal with an optical spectrometer or an optical spectrum analyzer to determine a wavelength of a spectral feature of the output optical signal.

39. The method of claim 32, wherein the input optical signal comprises a narrowband optical signal, the method further comprising measuring an intensity of the output optical signal with a photodetector.

40. The method of claim 32, wherein the optical element comprises an optical waveguide having a core and cladding substantially confining in at least one transverse dimension the input optical signal or the output optical signal, and the sensing region comprises a region of the optical waveguide having a volume for receiving the sample material in place of at least a portion of the core or the cladding.

41. The method of claim 40, wherein the optical waveguide comprises a slab waveguide arranged for substantially confining in one transverse dimension optical signals propagating in two dimensions therein, and at least a portion of the slab waveguide spatially overlaps at least a portion of the sensing region or at least a portion of the diffractive element set.

42. The method of claim 40, wherein the optical waveguide comprises a channel waveguide formed on a waveguide substrate and arranged for substantially confining in two transverse dimension optical signals propagating in one dimension therein, and at least a portion of the channel waveguide spatially overlaps at least a portion of the sensing region or at least a portion of the diffractive element set.

43. The method of claim 32, wherein the diffractive element set and the sensing region are arranged so that the spectral transformation information varies according to at least one optical property of the received sample material and the spatial transformation information is substantially invariant with respect to optical properties of the sample material.

44. The method of claim 32, wherein the diffractive element set and the sensing region are arranged so that the spatial transformation information varies according to at least one optical property of the received sample material and the spectral transformation information is substantially invariant with respect to optical properties of the sample material.

45. The method of claim 32, wherein the diffractive element set and the sensing region are arranged so that the spectral and spatial transformation information varies according to at least one optical property of the received sample material.

46. An optical apparatus, comprising an optical element having at least one set of diffractive elements and a sensing region, wherein:

the diffractive elements of the set are collectively arranged so as to comprise spectral and spatial transformation information;

the diffractive elements of the set are collectively arranged so as to transform at least a portion of an input optical signal into an output optical signal according to the spectral and spatial transformation information so that a spatial wavefront of the input optical signal differs from a spatial wavefront of the output optical signal, the input optical signal propagating from an input optical port, the output optical signal propagating to an output optical port, the input optical signal or the output optical signal propagating within the optical element so as to be successively incident on the diffractive elements of the set;

the sensing region is arranged for receiving a sample material so that the input optical signal or the output optical signal at least partly spatially overlaps a portion of the sample material in the sensing region; and the optical element is arranged so that the spatial and spectral transformation information is substantially invariant with respect to optical properties of the sample material.

47. An optical apparatus, comprising an optical element having at least one set of diffractive elements, a reference set of diffractive elements, and a sensing region, wherein:

the diffractive elements of the at least one set are collectively arranged so as to comprise spectral and spatial transformation information;

the diffractive elements of the at least one set are collectively arranged so as to transform at least a portion of an input optical signal into an output optical signal according to the spectral and spatial transformation information, the input optical signal propagating from an input optical port, the output optical signal propagating to an output optical port, the input optical signal or the output optical signal propagating within the optical element so as to be successively incident on the diffractive elements of the at least one set;

the sensing region is arranged for receiving a sample material so that the input optical signal or the output optical signal at least partly spatially overlaps a portion of the sample material in the sensing region; and the at least one set of diffractive elements and the sensing region are arranged so that the spectral or spatial transformation information varies according to at least one optical property of the received sample material;

the diffractive elements of the reference set are collectively arranged so as to comprise reference spectral and spatial transformation information;

the diffractive elements of the reference set are collectively arranged so as to transform at least a portion of a reference input optical signal into a reference output optical signal according to the reference spectral and spatial transformation information, the reference input optical signal propagating from a reference input optical port, the reference output optical signal propagating to a reference output optical port, the reference input optical signal or the reference output optical signal propagating within the optical element so as to be successively incident on the diffractive elements of the set; and the optical element is arranged so that the reference spatial and spectral transformation information is substantially invariant with respect to optical properties of the sample material.

48. The apparatus of claim 47, further comprising:

an optical source for launching the input optical signal into the optical element via the input optical port; and an optical receiver for receiving the output optical signal from the optical element via the output optical port.

49. A method, comprising:

receiving into a sensing region of an optical element a sample material;

receiving into the optical element via an input optical port an input optical signal, the optical element having at least one set of diffractive elements collectively arranged so as to comprise spectral and spatial transformation information, the diffractive elements of the set being collectively arranged so as to transform at least a portion of the input optical signal into an output optical signal according to the spectral and spatial transformation information, the input optical signal or the output optical signal propagating within the optical element so as to be successively incident on the diffractive elements of the set, the sensing region being arranged so that the input optical signal or the output optical signal at least partly spatially overlaps a portion of the sample material in the sensing region, the diffractive element set and the sensing region being arranged so that the spectral or spatial transformation information varies according to at least one optical property of the received sample material;

receiving from the optical element via an output optical port the output optical signal;

receiving into the optical element via a reference input optical port a reference input optical signal, the optical element having a reference set of diffractive elements collectively arranged so as to comprise reference spectral and spatial transformation information, the diffractive elements of the reference set being collectively arranged so as to transform at least a portion of the reference input optical signal into a reference output optical signal according to the reference spectral and spatial transformation information, the reference input optical signal or the reference output optical signal propagating within the optical element so as to be successively incident on the diffractive elements of the reference set, the diffractive element reference set and the sensing region being arranged so that the reference spectral and spatial transformation information is substantially invariant with respect to optical properties of the received sample material; and receiving from the optical element via a reference output optical port the reference output optical signal.

50. The method of claim 49, wherein the input optical signal and the reference input optical signal comprise a common broadband optical signal, the method further comprising measuring the output optical signal and the reference output optical signal with an optical spectrometer or an optical spectrum analyzer to compare a wavelength of a spectral feature of the output optical signal with a wavelength of a spectral feature of the reference output optical signal.

51. The method of claim 49, wherein the input optical signal comprises a first narrowband optical signal and the reference input optical signal comprises a second narrowband optical signal, the method further comprising measuring an intensity of the output optical signal with a signal photodetector and measuring the intensity of the reference output optical signal with a reference photodetector.

* * * * *